(12) United States Patent
Cottard et al.

(10) Patent No.: US 7,204,859 B2
(45) Date of Patent: Apr. 17, 2007

(54) COMPOSITION FOR THE OXIDATION DYEING OF KERATIN FIBERS, COMPRISING AT LEAST ONE FATTY ALCOHOL, AT LEAST ONE OXIDATION DYE, AT LEAST ONE ASSOCIATIVE POLYMER, AND AT LEAST ONE COMPOUND CHOSEN FROM FATTY ACID ESTERS AND METAL OXIDES

(75) Inventors: François Cottard, Courbevoie (FR); Christine Rondeau, Sartrouville (FR)

(73) Assignee: L'Oreal S.A., Paris (FR)

( * ) Notice: Subject to any disclaimer, the term of this patent is extended or adjusted under 35 U.S.C. 154(b) by 172 days.

(21) Appl. No.: 10/728,890

(22) Filed: Dec. 8, 2003

(65) Prior Publication Data

US 2004/0172771 A1    Sep. 9, 2004

Related U.S. Application Data

(60) Provisional application No. 60/502,967, filed on Sep. 16, 2003.

(30) Foreign Application Priority Data

Dec. 6, 2002   (FR)   .................. 02 15471

(51) Int. Cl.
*A61K 7/13*   (2006.01)
(52) U.S. Cl. .............. 8/405; 8/406; 8/408; 8/409; 8/410; 8/411; 8/412; 8/552; 8/554; 8/555; 8/558; 8/580; 8/611; 8/637.1
(58) Field of Classification Search ............ 8/405, 8/406, 408, 409, 410, 411, 412, 552, 554, 8/555, 558, 580, 611, 637.1
See application file for complete search history.

(56) References Cited

U.S. PATENT DOCUMENTS

| | | | | |
|---|---|---|---|---|
| 5,788,955 A | * | 8/1998 | Eteve et al. | ................ 424/60 |
| 2001/0023514 A1 | * | 9/2001 | Cottard et al. | ................ 8/406 |
| 2001/0023515 A1 | | 9/2001 | Cottard et al. | ................ 8/406 |
| 2002/0046431 A1 | * | 4/2002 | Laurent et al. | ................ 8/405 |

FOREIGN PATENT DOCUMENTS

| | | |
|---|---|---|
| EP | 1 142 555 | 10/2001 |
| EP | 1 142 556 | 10/2001 |
| EP | 1 413 287 A1 | 4/2004 |
| EP | 1 413 289 A1 | 4/2004 |
| WO | WO 02/45651 | 6/2002 |

OTHER PUBLICATIONS

English-language abstract for EP 1 413 287 A1, published Apr. 28, 2004, from the European Patent Office esp@cenet.
English-language abstract for EP 1 413 289 A1, published Apr. 28, 2004, from the European Patent Office esp@cenet.

* cited by examiner

Primary Examiner—Eisa Elhilo
(74) Attorney, Agent, or Firm—Finnegan, Henderson, Farabow, Garrett & Dunner, LLP

(57) ABSTRACT

Disclosed herein is a composition for the oxidation dyeing of keratin fibers, for example human keratin fibers, such as the hair, comprising, in a medium suitable for dyeing,
 a) at least one oxidation dye;
 b) at least one fatty alcohol;
 c) at least one associative polymer; and
 d) at least one compound chosen from fatty acid esters and metal oxides.

63 Claims, No Drawings

COMPOSITION FOR THE OXIDATION DYEING OF KERATIN FIBERS, COMPRISING AT LEAST ONE FATTY ALCOHOL, AT LEAST ONE OXIDATION DYE, AT LEAST ONE ASSOCIATIVE POLYMER, AND AT LEAST ONE COMPOUND CHOSEN FROM FATTY ACID ESTERS AND METAL OXIDES

This application claims benefit of U.S. Provisional Application No. 60/502,967, filed Sep. 16, 2003.

Disclosed herein is a composition for the oxidation dyeing of keratin fibers, for example of human keratin fibers, such as the hair, comprising at least one oxidation dye, at least one fatty alcohol, at least one associative polymer and at least one compound chosen from fatty acid esters and metal oxides.

It is known practice to dye keratin fibers, and in particular human hair, with dye compositions comprising oxidation dye precursors, generally known as "oxidation bases", such as ortho- and para-phenylenediamines, ortho- and para-aminophenols, and heterocyclic bases.

Oxidation dye precursors are compounds that may initially be uncolored or only weakly colored, which may develop their hair dyeing power in the presence of oxidizing agents, leading to the formation of colored compounds. The formation of these colored compounds may result either from an oxidative condensation of the "oxidation bases" with themselves or from an oxidative condensation of the "oxidation bases" with coloration modifiers, or "couplers", which may be present in the dye compositions used in oxidation dyeing and may be, for example, meta-phenylenediamines, meta-aminophenols, meta-diphenols, and certain heterocyclic compounds.

The variety of molecules that may be used, which comprise on the one hand the "oxidation bases" and on the other hand the "couplers", may allow a wide range of colors to be obtained.

Compositions which comprise oxidation dyes and are mixed before use with an oxidizing agent may be provided in the form of water-based creams, which may comprise fatty alcohols and occasionally soaps. These creams may have a high fatty alcohol content in order to ensure the consistency and stability of the medium.

It has been noted by the present inventors, however, that this high content of fatty alcohols may lead to a change in viscosity in the dyeing composition over time, which may be manifested in a reduction in the ease of mixing with the oxidizing agent or in an impairment of the usage qualities, such as for example elimination on rinsing.

However, after researching the question, the present inventors have found that oxidation dye compositions comprising at least one oxidation dye, at least one fatty alcohol, at least one associative polymer, and at least one compound chosen from fatty acid esters and metal oxides have a satisfactory consistency and a viscosity which may be stable over time without the need to increase the concentration of fatty alcohols.

Accordingly, disclosed herein is a composition for the oxidation dyeing of keratin fibers, for example human keratin fibers, such as the hair, comprising, in a medium suitable for dyeing,
 a) at least one oxidation dye;
 b) at least one fatty alcohol;
 c) at least one associative polymer; and
 d) at least one compound chosen from fatty acid esters and metal oxides.

Another embodiment relates to a ready-to-use composition for the dyeing of keratin fibers which comprises at least one oxidizing agent, at least one oxidation dye, at least one fatty alcohol, at least one associative polymer, and at least one compound chosen from fatty acid esters and metal oxides.

As used herein, the expression "ready-to-use composition" means a composition intended for application as it is to the keratin fibers; that is to say, it may be stored as it is before use or may result from the mixing of at least two compositions.

Also disclosed herein is a process for the oxidation dyeing of keratin fibers, for example human keratin fibers such as the hair, comprising applying to the fibers a composition (A) comprising, in a medium suitable for dyeing, at least one oxidation dye, at least one fatty alcohol, at least one associative polymer, and at least one compound chosen from fatty acid esters and metal oxides, the color being developed at alkaline, neutral or acidic pH, by means of a composition (B) comprising at least one oxidizing agent, which is mixed with the composition (A) at the time of use or which is applied sequentially before or after composition (A), optionally with intermediate rinsing.

Also disclosed herein are multi-compartment dyeing devices or multi-compartment kits for the oxidation dyeing of keratin fibers, for example human keratin fibers such as the hair. A device according to one embodiment may comprise a first compartment comprising at least one oxidation dye, at least one fatty alcohol, at least one associative polymer, and at least one compound chosen from fatty acid esters and at metal oxides, and a second compartment comprising at least one oxidizing agent.

Other features, aspects, subjects and advantages will emerge even more clearly on reading the description and the examples that follow.

The at least one fatty acid ester may be chosen from monoesters, diesters and triesters obtained from reacting linear or branched, saturated or unsaturated monoacids or diacids having 8 to 30 carbon atoms, which are optionally hydroxylated, with saturated or unsaturated, linear, branched or cyclic monoalcohols or polyols having 2 to 100 carbon atoms and having 1 to 30 hydroxyl groups.

The linear or branched, saturated or unsaturated monoacids or diacids may, for example, be chosen from stearic acid, palmitic acid, lauric acid, oleic acid, and myristic acid.

The saturated or unsaturated, linear, branched or cyclic monoalcohols or polyols may, for example, be chosen from ethanol, isopropanol, isooctanol, dodecanol, stearyl alcohol, ethylene glycol, propylene glycol, glycerol, polyethylene glycols, polypropylene glycols, glucose, methyl glucose, sorbitol, sorbitol anhydride, and pentaerythritol.

The saturated or unsaturated, linear, branched or cyclic monoalcohols or polyols may optionally be oxyalkylenated, for example oxyethylenated.

Examples of esters which may be used according to the invention include isopropyl myristate, stearyl stearate, ethylene glycol monostearate, ethylene glycol distearate, polyethylene glycol monostearates, polyethylene glycol distearates, sorbitan monopalmitate, glyceryl isostearate, propylene glycol dipelargonate, 2-ethylhexyl palmitate, sorbitan tristearate, di(2-ethylhexyl) sebacate, and glyceryl trihydroxystearate.

The at least one metal oxide may, for example, be chosen from aluminum oxides, zinc oxides, magnesium oxides, and titanium oxides.

The at least one metal oxide may, for example, be chosen from titanium oxides and mica-titanium oxide hybrid compounds.

Titanium oxides which may be used according to certain embodiments may have a particle size ranging from 2 to 500 nanometers, for example ranging from 2 to 300 nanometers, or for example from 2 to 50 nanometers.

The titanium oxides may be coated or uncoated.

Among uncoated titanium oxides mention may be made of the following products:

in powder form:

Bayertitan and Dioxyde de Titane A, offered by the company Bayer;

70110 Cardre UF TI02 offered by the company Cardre;
  in 10%, 20%, and 30% aqueous dispersion form with a particle size of 15, 20, and 60 nanometers:

Sunveil 1010, 1020, 1030, 2020, 2030, 6010, and 6030, offered by the company Catalysts & Chemicals; and Micro Titanium Dioxide—USP Grade offered by the company Color Techniques.

Among coated titanium oxides, mention may be made, for example, of the following products:
  titanium oxides coated with polydimethylsiloxane, such as Cardre Ultrafine Titanium Dioxide AS offered by the company Cardre;
  titanium oxides coated with polymethylhydrosiloxane, such as untreated, polymethylhydrosiloxane-coated titanium oxide sold under the trade name Cosmetic White SA-C47-051-10 by the company Myoshi;
  titanium oxides coated with perfluoropolymethyl isopropyl ether, such as Cardre Mica FHC 70173 and 70170 Cardre UF TI02 FHC, offered by the company Cardre;
  titanium oxides coated with silica, such as Spheritan AB offered by the company Catalysts & Chemicals;
  titanium oxides coated with polyester, such as Experimental Desoto Beads offered by the company Desoto;
  titanium oxides coated with chitosan, such as CT-2 Titanium Dioxide MT-500SA offered by the company Dainihon Kasei;
  titanium oxides coated with N-lauroyl-L-lysine, such as LL-5 Titanium Dioxide A 100, LL-3 Titanium Dioxide MT-100SA, LL-5 Titanium Dioxide CR-50, LL-5 Titanium Dioxide MT-100SA, and LL-5 Titanium Dioxide MT-500SA, offered by the company Dainihon Kasei;

The at least one compound chosen from fatty acid esters and metal oxides may be present in the composition in proportions ranging from 0.2% to 10%, or for example ranging from 0.5% and 5% by weight relative to the total weight of the composition.

The associative polymers are polymers whose molecules may be capable, in the formulation medium, of undergoing association with one another and/or with molecules of other compounds.

One example of associative polymers is amphiphilic polymers, i.e., polymers comprising at least one hydrophilic moiety which renders them soluble in water and at least one hydrophobic region comprising at least one fatty chain. By means of the at least one hydrophilic moiety and the at least one hydrophobic region, the polymers may interact and undergo assembly with one another and/or with other molecules.

The associative polymers according to certain embodiments may be chosen from non-ionic, anionic, cationic, and amphoteric associative polymers.

The associative polymers according to one embodiment may be chosen from associative polymers comprising at least one fatty chain. The at least one fatty chain may, for example, have from 8 to 30 carbon atoms, for example from 10 to 30 carbon atoms.

Among the anionic associative polymers comprising at least one fatty chain, mention may be made of:

(I) anionic associative polymers comprising at least one hydrophilic unit and at least one fatty-chain allyl ether unit, for example anionic associative polymers whose hydrophilic unit comprises at least one ethylenic unsaturated anionic monomer, or for example at least one acid chosen from vinylcarboxylic acid, acrylic acid, methacrylic acid, and mixtures thereof, the fatty-chain allyl ether unit of which corresponds to the monomer of formula (I) below:

in which R' is chosen from a hydrogen atom and a methyl group; B is an ethyleneoxy radical; n is chosen from an integer ranging from 0 to 100; and R is a hydrocarbon-based radical chosen from alkyl, arylalkyl, aryl, alkylaryl, and cycloalkyl radicals, having from 8 to 30 carbon atoms, for example from 10 to 24 carbon atoms, or for example from 12 to 18 carbon atoms. A unit of formula (I) according to one embodiment is a unit in which R' is a hydrogen atom, n is equal to 10, and R is a stearyl ($C_{18}$) radical.

Anionic amphiphilic polymers of this type are, for example, described and prepared according to an emulsion polymerization process in patent EP 0 216 479.

Among the fatty chain anionic associative polymers, in certain embodiments the polymers are formed from 20% to 60% by weight of acrylic acid and/or of methacrylic acid, from 5% to 60% by weight of lower alkyl (meth)acrylates, from 2% to 50% by weight of fatty-chain allyl ether of formula (I), and from 0% to 1% by weight of a crosslinking agent which is a well-known copolymerizable unsaturated polyethylenic monomer, for instance diallyl phthalate, allyl (meth)acrylate, divinylbenzene, (poly)ethylene glycol dimethacrylate, and methylenebisacrylamide.

Among the latter polymers, those according to certain embodiments may be crosslinked terpolymers of methacrylic acid, ethyl acrylate, and polyethylene glycol, such as 10 EO, and stearyl ether alcohol, such as Steareth-10, for example those sold by the company Allied Colloids under the names SALCARE SC 80® and SALCARE SC 90®, which are aqueous 30% emulsions of crosslinked terpolymers of methacrylic acid, ethyl acrylate and steareth-10 allyl ether, each unit comprising 40%, 50%, and 10%, respectively.

(II) anionic associative polymers comprising at least one hydrophilic unit of an unsaturated olefinic carboxylic acid, and at least one hydrophobic unit of an unsaturated carboxylic acid ($C_{10}$–$C_{30}$)alkyl ester.

These polymers may be chosen from those in which the hydrophilic unit of an unsaturated olefinic carboxylic acid corresponds to the monomer of formula (II) below:

in which R" is chosen from hydrogen, methyl, and ethyl, that is to say acrylic acid, methacrylic acid, and ethacrylic acid units, and in which the hydrophobic unit of an unsaturated carboxylic acid ($C_{10}$–$C_{30}$)alkyl ester may correspond to the monomer of formula (III) below:

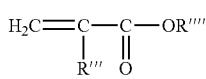 (III)

in which R''' is chosen from hydrogen, methyl, and ethyl, that is to say acrylate, methacrylate, and ethacrylate units, for example R''' is chosen from a hydrogen atom, that is to say acrylate units, and methyl, that is to say methacrylate units, and R'''' is $C_{10}$–$C_{30}$, for example, $C_{12}$–$C_{22}$ alkyl radical.

($C_{10}$–$C_{30}$) alkyl esters of unsaturated carboxylic acids according to certain embodiments may include, for example, lauryl acrylate, stearyl acrylate, decyl acrylate, isodecyl acrylate, dodecyl acrylate, and corresponding methacrylates, such as lauryl methacrylate, stearyl methacrylate, decyl methacrylate, isodecyl methacrylate, and dodecyl methacrylate.

Anionic polymers of this type are described and prepared, for example, in U.S. Pat. Nos. 3,915,921 and 4,509,949.

Among the anionic associative polymers of this type, those that may be used in accordance with certain embodiments include polymers formed from a monomer mixture comprising:
(i) at least one acrylic acid;
(ii) at least one ester of formula (III) described above in which R''' is chosen from hydrogen and methyl, and R'''' is chosen from alkyl radicals having from 12 to 22 carbon atoms;
(iii) and at least one crosslinking agent, which may be chosen from well-known copolymerizable polyethylenic unsaturated monomers, for instance diallyl phthalate, allyl (meth)acrylate, divinylbenzene, (poly)ethylene glycol dimethacrylates, and methylenebisacrylamide.

Among fatty-chain anionic associative polymers of this type, those that may be used in certain embodiments are those comprising from 60% to 95% by weight of acrylic acid, i.e., a hydrophilic unit, 4% to 40% by weight of $C_{10}$–$C_{30}$ alkyl acrylate, i.e., a hydrophobic unit, and 0% to 6% by weight of crosslinking polymerizable monomer, or for example those comprising from 96% to 98% by weight of acrylic acid, i.e., a hydrophilic unit, 1% to 4% by weight of $C_{10}$–$C_{30}$ alkyl acrylate, i.e., a hydrophobic unit, and 0.1.% to 0.6% by weight of crosslinking polymerizable monomer such as those described above.

Among the above-mentioned polymers, those that may be used according to certain embodiments include the products sold by the company Goodrich under the trade names PEMULEN® TR1, PEMULEN® TR2, and CARBOPOL® 1382, or for example, PEMULEN® TR1, and the product sold by the company SEPPIC under the name COATEX SX.

(III) maleic anhydride/$C_{30}$–$C_{38}$ α-olefin/alkyl maleate terpolymers, such as the product comprising maleic anhydride/$C_{30}$–$C_{38}$ α-olefin/isopropyl maleate copolymer and sold under the name Performa V 1608 by the company Newphase Technologies.

(IV) acrylic terpolymers comprising:
(a) 20% to 70% by weight of a carboxylic acid containing α,β-monoethylenic unsaturation;
(b) 20% to 80% by weight of a non-surfactant monomer containing α,β-monoethylenic unsaturation and being other than (a);
(c) 0.5% to 60% by weight of a non-ionic monourethane which is the product of reaction of a monohydric surfactant with a monoisocyanate containing monoethylenic unsaturation;

for example those described in patent application EP A 0 173 109, such as the terpolymer described in Example 3, namely a methacrylic acid/methyl acrylate/ethoxylated (40 EO) behenyl dimethyl-meta-isopropenylbenzylisocyanate terpolymer, as an aqueous 25% dispersion.

(V) copolymers comprising among their monomers at least one carboxylic acid containing α,β-monoethylenic unsaturation, at least one ester of a carboxylic acid containing α,β-monoethylenic unsaturation, and at least one oxyalkylenated fatty alcohol.

For example, these compounds may also comprise as a monomer at least one ester of a carboxylic acid containing α,β-monoethylenic unsaturation and at least one $C_1$–$C_4$ alcohol.

An example of a compound of this type which may be mentioned is ACULYN® 22 sold by the company Rohm & Haas, which is a methacrylic acid/ethyl acrylate/stearyl methacrylate oxyalkylenated terpolymer.

The non-ionic fatty-chain associative polymers used according to certain embodiments may be chosen from:
(1) celluloses modified with groups comprising at least one fatty chain, examples of which include:
hydroxyethylcelluloses modified with groups comprising at least one fatty chain, such as alkyl groups, arylalkyl groups, alkylaryl groups, and mixtures thereof, and in which the alkyl groups may for example be $C_8$–$C_{22}$, such as the product NATROSOL® Plus Grade 330 CS, which comprise $C_{16}$ alkyls, sold by the company Aqualon, or the product BERMOCOLL® EHM 100 sold by the company Berol Nobel; and
celluloses modified with at least one alkylphenyl polyalkylene glycol ether group, such as the product Amercell Polymer HM-1500, which is nonylphenyl polyethylene glycol (15) ether, sold by the company Amerchol.

(2) hydroxypropylguars modified with groups comprising at least one fatty chain, such as the product Esaflor HM 22, which comprises a $C_{22}$ alkyl chain, sold by the company Lamberti, and the products RE210-18, which comprises a $C_{14}$ alkyl chain, and RE205-1, which comprises a $C_{20}$ alkyl chain, sold by the company Rhône-Poulenc.

(3) copolymers of vinylpyrrolidone and of fatty-chain hydrophobic monomers, examples of which include:
the products Antaron V216 and Ganex V216, which comprises a vinylpyrrolidone/hexadecene copolymer, sold by the company I.S.P.
the products Antaron V220 and Ganex V220, which comprise avinylpyrrolidone/eicosene copolymer, sold by the company I.S.P.

(4) copolymers of $C_1$–$C_6$ alkyl methacrylates, of $C_1$–$C_6$ alkyl acrylates, and of amphiphilic monomers comprising at least one fatty chain, such as, for example, the oxyethylenated methyl acrylate/stearyl acrylate copolymer sold by the company Goldschmidt under the name ANTIL® 208.

(5) copolymers of hydrophilic methacrylates, of hydrophilic acrylates, and of hydrophobic monomers comprising at least one fatty chain, such as, for example, a polyethylene glycol methacrylate/lauryl methacrylate copolymer.

(6) polyurethane polyethers comprising in their chain both hydrophilic blocks, such as of a polyoxyethylenated nature and hydrophobic blocks which may be aliphatic sequences alone and/or cycloaliphatic and/or aromatic sequences.

(7) polymers with an aminoplast ether skeleton comprising at least one fatty chain, such as the PURE THIX® compounds sold by the company Sud-Chemie.

In certain embodiments, the polyurethane polyethers comprise at least two hydrocarbon-based lipophilic chains having from 8 to 30 carbon atoms, separated by a hydrophilic block, the hydrocarbon-based chains optionally being pendent chains or chains at the end of the hydrophilic block. For example, it is possible for at least one pendent chain to be included. In addition, the polymer may comprise a hydrocarbon-based chain at one end or at both ends of a hydrophilic block.

The polyurethane polyethers may be multiblock, such as in triblock form. Hydrophobic blocks may be at each end of the chain, for example triblock copolymers with a hydrophilic central block, or distributed both at the ends and in the chain, for example multiblock copolymers. These same polymers may also be graft polymers or starburst polymers.

The non-ionic fatty-chain polyurethane polyethers may be triblock copolymers in which the hydrophilic block is a polyoxyethylenated chain comprising from 50 to 1,000 oxyethylene groups. The non-ionic polyurethane polyethers may comprise a urethane linkage between the hydrophilic blocks, as the name indicates.

Also included among the non-ionic fatty-chain polyurethane polyethers are those in which the hydrophilic blocks are linked to the lipophilic blocks via other chemical bonds.

As examples of non-ionic fatty-chain polyurethane polyethers that may be used in certain embodiments, mention may also be made of RHEOLATE® 205 containing a urea function, sold by the company Rheox, and the RHEOLATES® 208, 204, and 212, and also ACRYSOL® RM 184, ACULYN® 46, and ACULYN® 44 from the company Rohm & Haas. ACULYN® 46 is a polycondensate of polyethylene glycol having 150 or 180 mol of ethylene oxide, of stearyl alcohol and of methylenebis(4-cyclohexyl isocyanate) (SMDI), at 15% by weight in a matrix of 4% maltodextrin and 81% water. ACULYN® 44 is a polycondensate of polyethylene glycol having 150 or 180 mol of ethylene oxide, of decyl alcohol and of methylenebis(4-cyclohexylisocyanate) (SMDI), at 35% by weight in a mixture of 39% propylene glycol and 26% water.

Mention may also be made of the product ELFACOS®T210 comprising a $C_{12-14}$ alkyl chain, and the product ELFACOS®T212 comprising a $C_{18}$ alkyl chain, from Akzo.

The product DW 1206B from Rohm & Haas comprising a $C_{20}$ alkyl chain and a urethane linkage, sold at a solids content of 20% in water, may also be used.

It is also possible to use solutions or dispersions of these polymers, for example in water or in aqueous alcoholic medium. Examples of such polymers that may be mentioned are RHEOLATE® 255, RHEOLATE® 278, and RHEOLATE® 244 sold by the company Rheox. The products DW 1206F and DW 1206J sold by the company Rohm & Haas may also be used. The polyurethane polyethers that may be used according to certain embodiments are for example described in the article by G. Formum, J. Bakke, and Fk. Hansen, Colloid Polym. Sci 271, 380.389 (1993).

The cationic fatty-chain associative polymers used in certain embodiments may be chosen from quaternized cellulose derivatives, polyacrylates comprising non-cyclic amine side groups, cationic polyurethanes, cationic polyvinyllactams, and acrylic terpolymers whose composition is given below.

The quaternized cellulose derivatives may be:

quaternized celluloses modified with at least one group comprising at least one fatty chain, such as alkyl, arylalkyl, and alkylaryl groups having at least 8 carbon atoms, and mixtures thereof;

quaternized hydroxyethylcelluloses modified with at least one group comprising at least one fatty chain, such as alkyl, arylalkyl, and alkylaryl groups having at least 8 carbon atoms, and mixtures thereof.

The alkyl radicals borne by the above quaternized celluloses or hydroxyethylcelluloses may have from 8 to 30 carbon atoms. The aryl radicals may denote phenyl, benzyl, naphthyl, and anthryl groups.

Examples of alkylhydroxyethylcelluloses quaternized with $C_8$–$C_{30}$ fatty chains that may be used include quaternized hydroxyethylcelluloses modified with a $C_{12}$ or $C_{18}$ alkyl group, such as the products QUATRISOFT® LM 200, QUATRISOFT® LM-X 529-18-A, QUATRISOFT® LM-X 529-18B, which is a $C_{12}$ alkyl, and QUATRISOFT® LM-X 529-8, which is a $C_{18}$ alkyl, and which are sold by the company Amerchol, and the products Crodacel QM, Crodacel QL, which is a $C_{12}$ alkyl, and Crodacel QS, which is a $C_{18}$ alkyl, and which are sold by the company Croda.

The polyacrylates comprising amine side groups, which may be quaternized or non-quaternized, may have, for example, stearth 20 hydrophobic groups, such as polyoxyethylenated (20) stearyl alcohol.

Examples that may be mentioned of polyacrylates comprising amine side chains include the polymers 8781-121 B or 9492-103 provided by the company National. Starch.

The cationic associative polyurethanes according to certain embodiments may be chosen from-cationic associative amphiphilic polyurethanes, which may be water-soluble or water-dispersible.

As used here, the term "water-soluble" or "soluble in water" in relation to the associative polyurethanes signifies that these polymers have a solubility in water at ambient temperature of at least 1% by weight; that is to say that, up to this concentration, no precipitate can be detected by the naked eye and the solution is clear and homogeneous.

As used herein, polyurethanes which are "water-dispersible" or "dispersible in water" are polymers which, when suspended in water, spontaneously form droplets having an average size, as measured by light scattering on a Coulter-type apparatus, ranging from 5 nm to 600 nm, for example from 5 nm to 500 nm.

The family of cationic amphiphilic polyurethanes according to certain embodiments disclosed herein has been described by the Applicant in French Patent Application No. 0 009 609; it may be represented by the general formula (Ia) below:

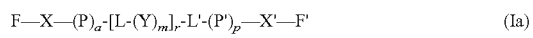

(Ia)

in which:

F and F', which may be identical or different, are chosen from hydrophobic groups and a hydrogen atom;

X and X', which may be identical or different, are chosen from groups comprising an amine function optionally having at least one of hydrophobic groups and groups L";

L, L', and L", which may be identical or different, are chosen from groups derived from diisocyanate;

P and P', which may be identical or different, are chosen from groups comprising an amine function optionally bearing at least one hydrophobic group;

Y is chosen from hydrophilic groups;

r is an integer ranging from 1 to 100, such as from 1 to 50, or 1 to 25; and a, m, and p, which may be identical or different, range from 0 to 1000; and wherein the molecule comprises at least one protonated or quaternized amine function and at least one hydrophobic group.

In one embodiment of polyurethanes, the only hydrophobic groups are the groups F and F' at the chain ends.

One family of cationic amphiphilic polyurethanes may correspond to formula (Ia) described above is as follows:

F and F' are each independently chosen from hydrophobic groups,

X and X' each represent a group L", a and p range from 1 to 1000, and

L, L', L", P, P', Y, and m have the meanings given above.

Another family of cationic amphiphilic polyurethanes may be the one corresponding to formula (Ia) above in which:

F and F' are each independently chosen from hydrophobic groups,

X and X' each represent a group L", a and p are 0, and

L, L', L", Y, P, P', and m have the meanings given above.

The fact that a and p are 0 means that these polymers do not comprise units derived from a monomer comprising at least one amine function, incorporated into the polymer during the polycondensation. The protonated amine functions of these polyurethanes may result from the hydrolysis of excess isocyanate functions, at the chain end, followed by alkylation of the primary amine functions formed with alkylating agents comprising at least one hydrophobic group, i.e., compounds of the type FQ or F'Q, in which F and F' are as defined above and Q denotes a leaving group such as those chosen from halides and sulphates.

Yet another family of cationic amphiphilic polyurethanes is the one corresponding to formula (Ia) above in which:

F and F' are both independently chosen from hydrophobic groups,

X and X' are both independently chosen from groups comprising at least one quaternary amine, a and p are 0, and L, L', Y, P, P', and m have the meanings given above.

The number-average molecular mass of the cationic associative polyurethanes may range from 400 to 500,000, for example from 1,000 to 400,000, or for example from 1,000 to 300,000.

As used herein, the expression "hydrophobic group" means a radical or polymer comprising at least one saturated or unsaturated, linear or branched hydrocarbon-based chain, which may comprise at least one heteroatom such as P, O, N, and S, or a radical comprising a perfluoro or silicone chain. When the hydrophobic group is a hydrocarbon-based radical, it may have at least 10 carbon atoms, for example 10 to 30 carbon atoms, or for example 12 to 30 carbon atoms or 18 to 30 carbon atoms. For example, the hydrocarbon-based group may be derived from a monofunctional compound.

By way of example, the hydrophobic group may be derived from a fatty alcohol such as stearyl alcohol, dodecyl alcohol, and decyl alcohol. It may also denote a hydrocarbon-based polymer such as, for example, polybutadiene.

When X and/or X' denote a group comprising a tertiary or quaternary amine, X and/or X' may represent one of the following formulae:

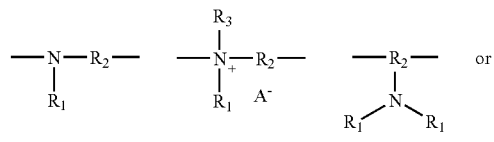

for X

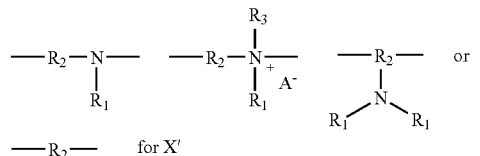

for X' in which:

$R_2$ is chosen from linear and branched alkylene radicals having from 1 to 20 carbon atoms, optionally comprising at least one of saturated rings, unsaturated rings, and arylene radicals, wherein at least one of the carbon atoms is optionally replaced with a heteroatom chosen from N, S, O, and P;

$R_1$ and $R_3$, which may be identical or different, are chosen from linear and branched $C_1$–$C_{30}$ alkyls, alkenyl radicals, and aryl radicals, wherein at least one of the carbon atoms is optionally replaced with a heteroatom chosen from N, S, O, and P; and $A^-$ is a physiologically acceptable counter-ion.

According to one aspect of the present disclosure, the groups L, L' and L" are chosen from a group of formula:

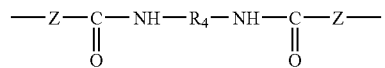

in which:

Z is chosen from oxygen atoms, sulfur atoms, and —NH groups; and $R_4$ is chosen from linear and branched alkylene radicals having from 1 to 20 carbon atoms, optionally comprising at least one of saturated rings, unsaturated rings, and arylene radicals, wherein at least one of the carbon atoms is optionally replaced with a heteroatom chosen from N, S, O, and P.

The groups P and P' comprising an amine function may represent at least one of the following formulae:

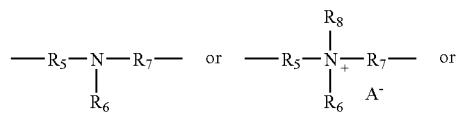

-continued

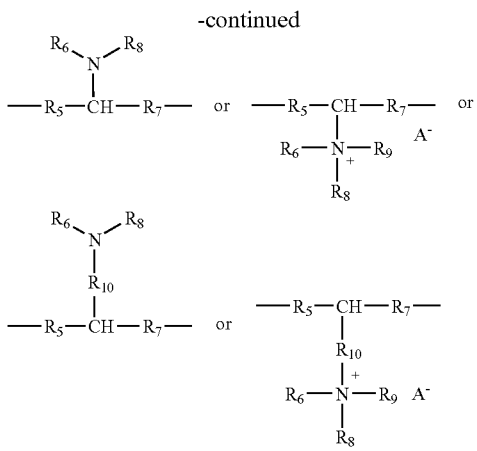

in which:
R$_5$ and R$_7$ have the same meanings as R$_2$ defined above;
R$_6$, R$_8$ and R$_9$ have the same meanings as R$_1$ and R$_3$ defined above;
R$_{10}$ is chosen from linear and branched, saturated and unsaturated alkylene groups which optionally comprising at least one heteroatom chosen from N, O, S, and P; and
A$^-$ is a physiologically acceptable counter-ion.

As regards the meaning of Y, as used herein the term "hydrophilic group" means a polymeric or non-polymeric water-soluble group.

By way of example, when Y is not a polymer, Y may be chosen from, by way of non-limiting example, ethylene glycol, diethylene glycol, and propylene glycol.

When Y is a hydrophilic polymer, in accordance with one embodiment, mention may be made, for example, of polyethers, sulphonated polyesters, sulphonated polyamides, and mixtures of these polymers. The hydrophilic compound may be a polyether, or for example a poly(ethylene oxide) or poly(propylene oxide).

The cationic associative polyurethanes of formula (Ia) according to certain embodiments may be formed from diisocyanates and from various compounds with functional groups comprising labile hydrogen. The functional groups comprising labile hydrogen may be chosen from alcohols, primary amines, secondary amines, and thiol functional groups giving, after reaction with diisocyanate functional groups, polyurethanes, polyureas, and polythioureas, respectively. The term "polyurethanes" as used herein encompasses these three types of polymers, namely polyurethanes, polyureas, and polythioureas, and also copolymers thereof.

A first type of compound involved in the preparation of the polyurethane of formula (Ia) is a compound comprising at least one unit comprising at least one amine functional group. This compound may be multifunctional, and the compound may be difunctional, that is to say that, according to one embodiment, this compound comprises two labile hydrogen atoms derived, for example, from hydroxyls, primary amines, secondary amines, or thiol functional groups. A mixture of multifunctional and difunctional compounds in which the percentage of multifunctional compounds is low may also be used.

As mentioned above, this compound may comprise more than one unit comprising at least one amine functional group. In this case, it may be a polymer that repeats the unit comprising at least one amine functional group.

Compounds of this type may be chosen from one of the following formulae:

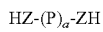

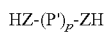

in which Z, P, P', a, and p are as defined above.

Examples of compounds comprising at least one amine functional group that may be mentioned include N-methyldiethanolamine, N-tert-butyldiethanolamine, and N-sulphoethyldiethanolamine.

The second compound involved in the preparation of the polyurethane of formula (Ia) is a diisocyanate corresponding to the formula:

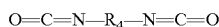

in which R$_4$ is as defined above.

By way of example, mention may be made of methylenediphenyl diisocyanate, methylenecyclohexane diisocyanate, isophorone diisocyanate, toluene diisocyanate, naphthalene diisocyanate, butane diisocyanate, and hexane diisocyanate.

A third compound involved in the preparation of the polyurethane of formula (Ia) may be a hydrophobic compound intended to form the terminal hydrophobic groups of the polymer of formula (Ia).

This compound comprises a hydrophobic group and a functional group comprising at least one labile hydrogen, for example hydroxyls, primary amines, secondary amines, and thiol functional groups.

By way of example, this compound may be a fatty alcohol such as stearyl alcohol, dodecyl alcohol, and decyl alcohols. When this compound comprises a polymeric chain, it may be, for example, α-hydroxylated hydrogenated polybutadiene.

The hydrophobic group of the polyurethane of formula (Ia) may also result from the quaternization reaction of the tertiary amine of the compound comprising at least one tertiary amine unit. Thus, the hydrophobic group may be introduced via the quaternizing agent. This quaternizing agent may be a compound of the type FQ or F'Q, in which F and F' are as defined above and Q is chosen from leaving groups such as halides and sulphates.

The cationic associative polyurethane may also comprise a hydrophilic block. This block is provided by a fourth type of compound involved in the preparation of the polymer. This fourth compound may be multifunctional. The fourth compound may, for example, be difunctional. It is also possible to have a mixture in which the percentage of multifunctional compounds is low.

The functional groups comprising at least one labile hydrogen may be chosen from alcohols, primary amines, secondary amines, and thiol functional groups. This fourth compound may be a polymer terminated at the chain ends with one of these functional groups comprising at least one labile hydrogen.

By way of example, when the fourth compound is not a polymer, it may be chosen from, by way of non-limiting example, ethylene glycol, diethylene glycol, and propylene glycol.

When the fourth compound is a hydrophilic polymer, mention may be made, for example, of polyethers, sulphonated polyesters, sulphonated polyamides, and mixtures of these polymers. The hydrophilic compound may be chosen from polyethers, or for example, poly(ethylene oxide) and poly(propylene oxide).

The hydrophilic group Y in formula (Ia) is optional. Specifically, the units comprising a quaternary amine or protonated functional group may suffice to provide the solubility or water-dispersibility required for this type of polymer in an aqueous solution.

Although the presence of hydrophilic group Y is optional, cationic associative polyurethanes comprising such a group may be used in certain embodiments.

The said cationic associative polyurethanes may be water-soluble or water-dispersible.

The cationic poly(vinyllactam) polymers according to the invention comprise:
a) at least one monomer chosen from vinyllactam monomers and alkylvinyllactam monomers;
b) at least one monomer chosen from structures (Ib) and (IIb) below:

$$H_2C=C(R11)-C(=O)-X''-(Y')_{p'}-(CH_2CH_2O)_{m'}-(CH_2CH(R12)O)_{n'}-(Y1)_q-\overset{+}{N}(R13)(R14)(R15) \quad Z^- \quad (Ib)$$

$$H_2C=C(R11)-C(=O)-X''-(Y')_{p'}-(CH_2CH_2O)_{m'}-(CH_2CH(R12)O)_{n'}-(Y1)_q-N(R13)(R14) \quad (IIb)$$

(IIb)

in which:
X'' is chosen from oxygen atoms and NR16 radicals,
R11 and R16, which may be identical or different, are chosen from a hydrogen atom, linear $C_1$–$C_5$ alkyl radicals, and branched $C_1$–$C_5$ alkyl radicals,
R12 is chosen from linear $C_1$–$C_4$ alkyl radicals and branched $C_1$–$C_4$ alkyl radicals,
R13, R14, and R15, which may be identical or different, are chosen from a hydrogen atom, linear $C_1$–$C_{30}$ alkyl radicals, branched $C_1$–$C_{30}$ alkyl radicals, and radicals of formula (IIIb):

$$-(Y2)_r-(CH_2-CH(R17)-O)_x-R18 \quad (IIIb)$$

in which:
Y', Y1, and Y2, which may be identical or different, are chosen from linear $C_2$–$C_{16}$ alkylene radicals and branched $C_2$–$C_{16}$ alkylene radicals,
R17 is chosen from a hydrogen atom, linear $C_1$–$C_4$ alkyl radicals, branched $C_1$–$C_4$ alkyl radicals, linear $C_1$–$C_4$ hydroxyalkyl radicals, and branched $C_1$–$C_4$ hydroxyalkyl radicals,
R18 is chosen from hydrogen atoms, linear $C_1$–$C_{30}$ alkyl radicals, and branched $C_1$–$C_{30}$ alkyl radicals,
p', q, and r', which may be identical or different, are chosen from 0 and 1,
m' and n', which may be identical or different, are each an integer ranging from 0 to 100,
x is an integer ranging from 1 to 100, and
Z is chosen from organic and mineral acid anions,
with the proviso that:
at least one of the substituents R13, R14, R15, and R18 is chosen from linear $C_9$–$C_{30}$ alkyl radicals and branched $C_9$–$C_{30}$ alkyl radicals,
if m or n is not zero, then q is equal to 1, and
if m or n are equal to zero, then p' or q is equal to 0.

The cationic poly(vinyllactam) polymers according to certain embodiments may be crosslinked or non-crosslinked, and may also be block polymers.

For example, the counter-ion $Z^-$ of the monomers of formula (Ib) may be chosen from halide ions, phosphate ions, methosulphate ions, and tosylate ions.

As another example, R13, R14, and R15, which may be identical or different, are chosen from a hydrogen atom, linear $C_1$–$C_{30}$ alkyl radicals, and branched $C_1$–$C_{30}$ alkyl radicals.

As yet another example, the monomer b) is a monomer of formula (Ib) for which m and n are equal to zero.

The vinyllactam or alkyvinyllactam monomer may be a compound of structure (IVb):

$$CH(R19)=C(R20)-N\underset{(CH_2)_s}{\overset{\diagup}{\diagdown}}=O \quad (IVb)$$

in which:
s is an integer ranging from 3 to 6,
R19 is chosen from a hydrogen atom and $C_1$–$C_5$ alkyl radicals, and
R20 is chosen from a hydrogen atom and $C_1$–$C_5$ alkyl radicals,
with the proviso that at least one of the radicals R19 and R20 is a hydrogen atom.

For example, the monomer (IVb) may be vinylpyrrolidone.

The cationic poly(vinyllactam) polymers according to certain embodiments may also comprise at least one additional monomer, which may be cationic or non-ionic.

As compounds that may be used according to certain embodiments, mention may be made of the following terpolymers comprising at least:
(a) a monomer of formula (IVb),
(b) a monomer of formula (Ib) in which p is equal to 1, q is equal to 0, R13 and R14, which may be identical or different, are chosen from a hydrogen atom and $C_1$–$C_5$ alkyl radicals, and R15 is chosen from $C_9$–$C_{24}$ alkyl radicals, and
(c) a monomer of formula (IIb) in which R13 and R14, which may be identical or different, are chosen from a hydrogen atom and $C_1$–$C_5$ alkyl radicals.

For example, terpolymers comprising, on a weight basis, from 40% to 95% of monomer (a), 0.1% to 55% of monomer (c), and 0.25% to 50% of monomer (b) may be used.

Such polymers are described in patent application WO 00/68282, the content of which is incorporated by reference herein.

Cationic poly(vinyllactam) polymers according to certain embodiments that may be used include vinylpyrrolidone/dimethylaminopropylmethacrylamide/dodecyldimethylmethacrylamidopropylammonium tosylate terpolymers, vinylpyrrolidone/dimethylaminopropylmethacrylamide/cocoyldimethylmethacrylamidopropylammonium tosylate terpolymers, and vinylpyrrolidone/dimethylaminopropyl methacrylamide/lauryld imethylmethacrylamidopropylammonium tosylate and chloride terpolymers.

The weight-average molecular mass of the cationic poly(vinyllactam) polymers according to this embodiment may range from 500 to 20,000,000. It may, for example, range from 200,000 to 2,000,000, or for example from 400,000 to 800,000.

Among the cationic amphiphilic polymers according to this embodiment, mention may also be made of acrylic terpolymers as described in patent application EP 1 090 623 and which comprise:

from 5% to 80% by weight, such as from 15% to 70% by weight or from 40% to 70% by weight of an acrylate monomer (a) chosen from $C_1$–$C_6$ alkyl acrylates and $C_1$–$C_6$ alkyl methacrylates;

from 5% to 80% by weight, for example from 10% to 70% by weight or for example from 20% to 60% by weight, of a monomer (b) chosen from heterocyclic vinyl compounds comprising at least one atom chosen from nitrogen atoms and sulphur atoms, (meth)acrylamides, mono- and di($C_1$–$C_4$)alkylamino($C_1$–$C_4$)alkyl (meth)acrylates, and mono- or di($C_1$–$C_4$)alkylamino($C_1$–$C_4$) alkyl(meth)acrylamides;

from 0.1% to 30% by weight, for example from 0.1% to 10% by weight, of a monomer (c) chosen from at least one of:

(i) urethane produced by reaction between monoethylenic unsaturated isocyanate and at least one non-ionic surfactant with a $C_{1-4}$ alkoxy end;

(ii) block copolymers of 1,2-butylene oxide and of 1,2-ethylene oxide;

(iii) copolymerizable ethylenic unsaturated surfactant monomers obtained by condensation of at least one non-ionic surfactant with at least one of α,β-ethylenic unsaturated carboxylic acid and its anhydride;

(iv) surfactant monomers chosen from the products of reactions such as the reaction of at least one urea of monoethylenic unsaturated monoisocyanate with at least one non-ionic surfactant comprising at least one amine functional group;

(v) (meth)allyl ether of formula $CH_2$=$CR21CH_2O$ $(A2)_{m'}(B2)_{n'}(A2)_{p'}R22$ in which R21 is chosen from a hydrogen atom and a methyl group, A2 is chosen from propylenoxy and butylenoxy groups, B2 denotes ethylenoxy, n' is chosen from an integer ranging from 0 to 200, for example less than 100, m' and p' are chosen from zero or an integer less than n, and R22 is a hydrophobic group containing at least 8 carbon atoms, for example a $C_8$–$C_{30}$ group; and (vi) urethane non-ionic monomers produced by reaction of at least one monohydric non-ionic surfactant with at least one monoethylenic unsaturated isocyanate; wherein the weight percentages of monomers is based on the total weight of the monomers comprising the terpolymer.

Acrylate monomers (a) that may be used comprise $C_2$–$C_6$ alkyl acrylates. Ethyl acrylate, for example, may be used.

Examples of monomers (b) which should be mentioned are N,N-dimethylaminoethyl methacrylate (DMAEMA), N,N-diethylaminoethyl acrylate, N,N-diethylaminoethyl methacrylate, N-t-butylaminoethyl acrylate, N-t-butylaminoethyl methacrylate, N,N-dimethylamino-propylacrylamide, N,N-dimethylaminopropylmethacrylamide, N,N-diethylaminopropylacrylamide, and N,N-diethylaminopropylmethacrylamide. N,N-dimethylaminoethyl methacrylate, for example, may be used.

The monomers (c) may be copolymerizable ethylenic unsaturated surfactant monomers obtained by condensing at least one non-ionic surfactant with at least one of α,β-ethylenic unsaturated carboxylic acid and its anhydride, for example $C_3$–$C_4$ mono- and dicarboxylic acids and their anhydrides or for example acrylic acid, methacrylic acid, crotonic acid, maleic acid, maleic anhydride, itaconic acid, and itaconic anhydride.

Examples of monomers (c) that may be used correspond to copolymerizable ethylenic unsaturated surfactant monomers obtained by condensing at least one non-ionic surfactant with itaconic acid. Among the non-ionic surfactants which may be mentioned are $C_{10}$–$C_{30}$ fatty alcohols alkoxylated with 2 to 100 mol, for example from 5 to 50 mol of an alkylene oxide, such as, for example, polyethylene glycol ethers of $C_{10}$–$C_{30}$ fatty alcohols and polyethylene glycol ethers of cetyl alcohol, which are called CETETH in the CTFA dictionary, 7th edition, 1997.

Acrylic terpolymers may thus be chosen from acrylic terpolymers comprising acrylates, amino (meth)acrylates, and $C_{10}$–$C_{30}$ alkyl itaconate, polyoxyethylenated with 20 mol of ethylene oxide.

Conventional methods for preparing these acrylic terpolymers are known to those skilled in the art. Such methods include solution polymerization, precipitation polymerization, and emulsion polymerization. Terpolymers in accordance with certain embodiments and methods for preparing them are described for example in patent applications EP A 0 824 914 and EP A 0 825 200.

Among these terpolymers, a STRUCTURE® 7 Plus polymer sold by the company National Starch may be used, which comprises acrylates, amino (meth)acrylates, and $C_{10}$–$C_{30}$ alkyl itaconate, polyoxyethylenated with 20 mol of ethylene oxide, in the form of an aqueous dispersion comprising 20% active material.

In addition to these monomers, the terpolymers can comprise other monomers which allow the said terpolymers to be crosslinked. These monomers may be used in relatively low proportions, of up to 2% by weight relative to the total weight of the monomers used to prepare the terpolymers. Such crosslinking monomers may comprise aromatic monomers bearing several vinyl substituents, alicyclic monomers bearing several vinyl substituents, bifunctional esters of phthalic acid, bifunctional esters of methacrylic acid, multifunctional esters of acrylic acid, and N-methylenebisacrylamide and aliphatic monomers bearing several vinyl substituents such as dienes, trienes, and tetraenes.

Crosslinking monomers may be, for example, divinylbenzenes, trivinylbenzenes, 1,2,4-trivinylcyclohexene, 1,5-hexadiene, 1,5,9-decatriene, 1,9-decadiene, 1,5-heptadiene, diallyl phthalates, ethylene glycol dimethacrylate, polyethylene glycol dimethacrylates, penta- and tetraacrylates, tri-allyl pentaerythritols, octaallyl sucroses, cycloparaffins, cycloolefins, and N-methylenebisacrylamide.

The associative polymers according to certain embodiments may also be chosen from amphoteric associative polymers.

As used herein, the term "amphoteric polymers" generally denotes polymers which comprise units K and M randomly distributed in the polymer chain, where K denotes a unit derived from a monomer comprising at least one basic nitrogen atom and M denotes a unit deriving from an acidic monomer comprising at least one carboxylic or sulphonic groups, or else K and M may denote groups derived from zwitterionic carboxybetaine or sulphobetaine monomers;

K and M may also denote a cationic polymer chain comprising at least one of primary, secondary, tertiary, and quaternary amine groups, in which at least one of the amine groups bears a carboxylic or sulphonic group linked via a hydrocarbon-based radical, or else K and M form part of a chain of a polymer comprising an α,β-dicarboxylic ethylene unit in which one of the carboxylic groups has been made to react with a polyamine comprising at least one of primary and secondary amine groups.

The amphoteric polymers used according to certain embodiments may further comprise at least one fatty chain having 8 to 30 carbon atoms, and may be chosen, for example, from polymers derived from polyaspartic acid and comprising at least one fatty chain having 8 to 30 carbon atoms, such as those:

described and prepared in patent application EP 0 767 191, the content of which is incorporated by reference herein. Such polymers may be prepared in conventional manner by reacting polysuccinimide (PSI) with fatty-chain ($C_8$–$C_{24}$) amines in a solvent medium in the presence or absence of a basic catalyst such as, for example, aliphatic tertiary amines, followed by amphoterization of the resultant product by reaction with a halogenated organic acid.

Among the $C_8$–$C_{24}$ fatty-chain amines which are reacted with the PSI, mention may be made of octylamine, nonylamine, decylamine, dodecylamine, tetradecylamine, hexadecylamine, octadecylamine, octadecenylamine, eicosyldecylamine, octynylamine, decenylamine, dodecenylamine, tetradecenylamine, hexadecenylamine, octadecenylamine, and eicosenylamine.

Examples of such polymers may be prepared by reacting PSI with n-laurylamine or with n-stearylamine in the presence of N,N-dimethyl-1,3-propanediamine as a basic catalyst, followed by amphoterization of the resultant product by reaction with potassium monochloroacetate. These polymers are prepared with greater details on pages 13 to 20 (lines 1–4) and in Examples 1 to 5 on pages 28 to 34 (lines 1–4) of the above-referenced patent application EP 0 767 191.

described and prepared in patent application EP 0 884 344, the contents of which are incorporated by reference herein. These polymers may be prepared by reacting gaseous ammonia with at least one $C_8$–$C_{24}$ alkyl or alkenyl monomaleate in a solvent medium under reduced pressure at a temperature ranging from 120° C. to 140° C. for from 4 to 6 hours.

The $C_8$–$C_{24}$ alkyl or alkenyl radicals may be chosen from the following linear or branched radicals: decyl, dodecyl, tetradecyl, hexadecyl, octadecyl, and oleyl.

Examples of such polymers include polymers comprising aspartic acid units and decyl aspartate units, polymers comprising aspartic acid units and dodecyl aspartate units, polymers comprising aspartic acid units and cetyl aspartate units, polymers comprising aspartic acid units and stearyl aspartate units, and polymers comprising aspartic acid units and n-decylaspartamide units, which are described in Examples 1 to 6 in the above-referenced patent application EP 0 884 344.

described and prepared in patent application EP 0 959 094, the contents of which is incorporated by reference herein. These polymers may be prepared by reacting, in a solvent medium, gaseous ammonia with a maleic acid monoamide, polyoxyalkylenated, and hydrophobically modified by a linear or branched $C_8$–$C_{30}$ alkyl or alkenyl chain, optionally in a mixture with at least one monoester of maleic acid.

An example of a polymer thus prepared is described in Example 2 on page 11 of the above-referenced patent application EP 0 959 094.

described and prepared in patent application EP 0 959 090, the contents of which are incorporated by reference herein. These hydrophobically modified polymers of high molecular weight may be obtained from derivatives of maleic acid and gaseous ammonia and difunctional or polyfunctional amines or alcohols.

Examples of copolymers comprising aspartic acid units and cetyl aspartate units or comprising aspartic acid units and cetyl aspartate units are given, respectively, in Examples 3 and 5 of the above-referenced patent application EP 0 959 090.

described and prepared in patent application EP 0 959 091, the contents of which are incorporated by reference herein. These hydrophobically modified polymers may be prepared from maleic acid monoester or monoamide and gaseous ammonia.

Examples of such copolymers are given in Examples 1, 2, 3 and 5 of the above-referenced patent application EP 0 959 091.

According to certain embodiments, the amphoteric polymers comprising at least one fatty chain having 8 to 30 carbon atoms may be chosen from polymers comprising at least one non-cyclic cationic unit. For example, the polymers may be used which are prepared from or comprise from 1 to 20 mol % of at least one monomer comprising a fatty chain, such as 1.5 to 15 mol % or 1.5 to 6 mol %, relative to the total number of moles of monomers.

The said fatty-chain amphoteric polymers that may be used according to certain embodiments comprise, or are prepared by copolymerizing:

1) at least one monomer of formula (Va) or (Vb):

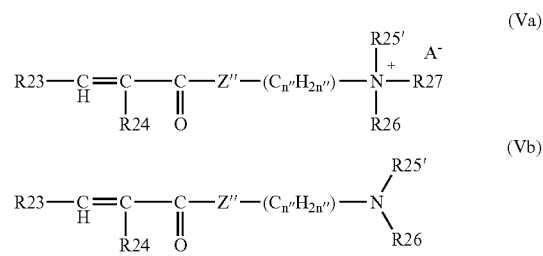

in which R23 and R24, which may be identical or different, are chosen from a hydrogen atom and a methyl radical, R25', R26 and R27, which may be identical or different, are chosen from linear and branched alkyl radicals having from 1 to 30 carbon atoms, Z'' is chosen from NH groups and an oxygen atom, n'' is an integer ranging from 2 to 5, and A$^-$ is an anion derived from a compound chosen from organic acids and mineral acids, such as methosulphate anions, and halides such as chloride and bromide;

2) at least one monomer of formula (VI)

(VI)

in which R28 and R29, which may be identical or different, are chosen from a hydrogen atom and a methyl radical; and 3) at least one monomer of formula (VII):

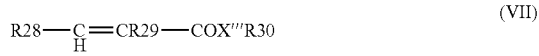
(VII)

in which R28 and R29, which may be identical or different, are chosen from a hydrogen atom and a methyl radical, X''' is chosen from oxygen and nitrogen atoms, and R30 is chosen from linear and branched alkyl radicals having from 1 to 30 carbon atoms; wherein at least one of the monomers of formula (Va), (Vb) and (VII) comprises at least one fatty chain.

The monomers of formulae (Va) and (Vb) of the present invention may be chosen from the group comprising:

dimethylaminoethyl methacrylate, dimethylaminoethyl acrylate, diethylaminoethyl methacrylate, diethylaminoethyl acrylate, dimethylaminopropyl methacrylate, dimethylaminopropyl acrylate, dimethylaminopropylmethacrylamide, and dimethylaminopropylacrylamide, and these monomers optionally being quaternized, for example with a $C_1$–$C_4$ alkyl halide or a $C_1$–$C_4$ dialkyl sulphate.

For example, the monomer of formula (Va) may be chosen from acrylamidopropyltrimethylammonium chloride and methacrylamidopropyltrimethylammonium chloride.

The monomers of formula (VI) disclosed herein are may be chosen from acrylic acid, methacrylic acid, crotonic acid, and 2-methylcrotonic acid. For example, the monomer of formula (VI) may be acrylic acid.

The monomers of formula (VII) disclosed herein may be chosen from $C_{12}$–$C_{22}$, for example $C_{16}$–$C_{18}$ alkyl acrylates and methacrylates.

The monomers comprising the fatty-chain amphoteric polymers disclosed herein may be already neutralized and/or quaternized.

The ratio of the number of cationic charges/anionic charges may be equal to 1.

The fatty-chain amphoteric polymers according to certain embodiments may comprise from 1 mol % to 10 mol % of the monomer comprising a fatty chain, such as the monomer of formula (Va), (Vb) or (VII)), for example from 1.5 mol % to 6 mol %.

The weight-average molecular weights of the fatty-chain amphoteric polymers according to certain embodiments may range from 500 to 50,000,000, for example from 10,000 to 5,000,000.

The fatty-chain amphoteric polymers according to the present disclosure may also comprise other monomers such as non-ionic monomers, such as $C_1$–$C_4$ alkyl acrylates and methacrylates.

Fatty-chain amphoteric polymers according to the present disclosure are described and prepared, for example, in patent application WO 98/44012.

Among the fatty-chain amphoteric polymers according to certain embodiments, mention may be made of acrylic acid/(meth)acrylamidopropyltrimethylammonium chloride/stearyl methacrylate terpolymers.

In the oxidation dyeing composition disclosed herein, at least one cationic or non-ionic associative polymer may be used, for example a cationic associative polymer. In one embodiment, the associative polymer is chosen from cationic polyurethanes.

The associative polymer or polymers may be present in the composition in amounts by weight ranging from 0.05% to 10%, for example from 0.1% to 5% of the total weight of the composition.

The ratio by weight of the at least one compound chosen from fatty acid esters and metal oxides to the at least one associative polymer may range from 0.1 to 10, for example from 0.5 to 5.

The at least one fatty alcohol according to certain embodiments may be non-oxyalkylenated and non-glycerolated, linear or branched, saturated or unsaturated, and have 8 to 40 carbon atoms. By way of example mention may be made of cetyl alcohol, stearyl alcohol, and oleyl alcohol.

The at least one fatty alcohol may be oxyalkylenated or glycerolated.

By oxyalkylenated fatty alcohol as used herein is meant any pure fatty alcohol of the following structure:

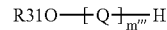

in which:

R31 is chosen from saturated and unsaturated, linear and branched radicals having 8 to 40 carbon atoms, such as 8 to 30 carbon atoms, Q is chosen from oxyethylenated radicals (i), oxypropylenated radicals (ii)$_1$, and oxypropylenated radicals (ii)$_2$, of the following respective formulae:

(i)

(ii)$_1$

(ii)$_2$ m''' represents the number of ethylene oxide groups (i) and/or propylene oxide groups (ii)$_1$ or (ii)$_2$, which may range from 1 to 250, such as from 2 to 100.

As used herein, by glycerolated fatty alcohol is meant any pure fatty alcohol of the following structure:

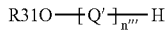

in which

R31 is chosen from saturated or unsaturated, linear or branched radicals having 8 to 40 carbon atoms, such as 8 to 30 carbon atoms, Q' represents a glycerolated radical (iii) of the following formula:

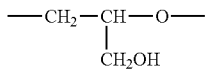

n''' represents the number of glycerol groups (iii) and may range from 1 to 30, such as from 1 to 10.

Oxyalkylenated fatty alcohols which may be used according to certain embodiments may be chosen from saturated and unsaturated, linear and branched fatty alcohols having 10 to 20 carbon atoms and from 2 to 40 ethylene oxide groups.

As examples of oxyalkylenated fatty alcohol compounds, mention may be made of the following commercialized products:

MERGITAL® LM2 [lauryl alcohol 2 EO], sold by the company Cognis;

Ifralan L12, sold by the company Ifrachem and REWO-PAL® 12, sold by Goldschmidt, [lauryl alcohol 12 EO];

EMPILAN® KA 2.5/90FL, sold by Albright & Wilson, and MERGITAL® BL309, sold by Cognis [decyl alcohol 3 EO];

EMPILAN® KA 5/90 FL, sold by Albright & Wilson, and MERGITAL® BL589, sold by Cognis [decyl alcohol 5 EO];

BRIJ® 58, sold by Uniqema, and Simusol 58, sold by SEPPIC [cetyl alcohol 20 EO];

Emulgin 05, sold by Cognis [oleocetyl alcohol 5 EO];

MERGITAL® OC30, sold by Cognis [oleocetyl alcohol 30 EO];

BRIJ® 72, sold by Uniqema [stearyl alcohol 2 EO];

BRIJ® 76, sold by Uniqema [stearyl alcohol 10 EO];

BRIJ® 78P, sold by Uniqema [stearyl alcohol 20 EO];

BRIJ® 700, sold by Uniqema [stearyl alcohol 100 EO];

Emulgin B1, sold by Cognis [cetylstearyl alcohol 12 EO];

Emulgin L, sold by Cognis [cetyl alcohol 9 EO and 2 PO]; and

Witconol APM, sold by Goldschmidt [myristyl alcohol 3 PO].

As examples of glycerolated fatty alcohol compounds, mention may be made of lauryl alcohol comprising 4 mol of glycerol, which has an INPCI name of polyglyceryl-4 lauryl ether, oleyl alcohol comprising 4 mol of glycerol, which has an INPCI name of polyglyceryl-4 oleyl ether, oleyl alcohol comprising 2 mol of glycerol, which has an INPCI name of polyglyceryl-2 oleyl ether, cetearyl alcohol comprising 2 mol of glycerol, cetearyl alcohol comprising 6 mol of glycerol, oleocetyl alcohol comprising 6 mol of glycerol, and octadecanol comprising 6 mol of glycerol.

The at least one fatty alcohol may represent a mixture of fatty alcohols, which means that, in a commercial product, a plurality of species of fatty alcohols may coexist in the form of a mixture.

The at least one fatty alcohol may be present in the composition in proportions by weight ranging from 0.05% to 30%, such as from 0.5% to 20% of the total weight of the composition.

The at least one oxidation dye that may be used in accordance with the present disclosure may be chosen from oxidation bases and couplers.

The compositions disclosed herein may comprise at least one oxidation base.

The oxidation bases that may be used in the context of present disclosure may be chosen from those conventionally used in oxidation dyeing, and among which mention may be made of ortho- and para-phenylenediamines, double bases, ortho- and para-aminophenols, heterocyclic bases, and the acid addition salts thereof.

Mention may also be made of:

(I) the para-phenylenediamines of formula (XI) below, and the acid addition salts thereof:

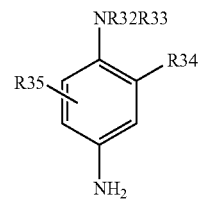

in which:

R32 is chosen from a hydrogen atom, $C_1$–$C_4$ alkyl radicals, $C_1$–$C_4$ monohydroxyalkyl radicals, $C_2$–$C_4$ polyhydroxyalkyl radicals, ($C_1$–$C_4$)alkoxy($C_1$–$C_4$)alkyl radicals, and $C_1$–$C_4$ alkyl radicals substituted with at least one of nitrogenous, phenyl, and 4'-aminophenyl groups;

R33 is chosen from a hydrogen atom, $C_1$–$C_4$ alkyl radicals, $C_1$–$C_4$ monohydroxyalkyl radicals, $C_2$–$C_4$ polyhydroxyalkyl radicals, ($C_1$–$C_4$)alkoxy($C_1$–$C_4$)alkyl radicals, and $C_1$–$C_4$ alkyl radicals substituted with at least one nitrogenous group;

R32 and R33 may also form, together with the nitrogen atom to which they are attached, a 5- or 6-membered nitrogen heterocycle optionally substituted with at least one of alkyl, hydroxyl, and ureido groups;

R34 is chosen from a hydrogen atom, halogen atoms such as chlorine atom, $C_1$–$C_4$ alkyl radicals, sulpho radicals, carboxyl radicals, $C_1$–$C_4$ monohydroxyalkyl radicals, $C_1$–$C_4$ hydroxyalkoxy radicals, acetylamino($C_1$–$C_4$)alkoxy radicals, mesylamino($C_1$–$C_4$)alkoxy radicals, and carbamoylamino($C_1$–$C_4$)alkoxy radicals, R35 is chosen from a hydrogen atom, halogen atoms, and $C_1$–$C_4$ alkyl radicals.

Among the nitrogenous groups of formula (XI) above, mention may be made of amino, mono($C_1$–$C_4$)alkylamino, di($C_1$–$C_4$)alkylamino, tri($C_1$–$C_4$)alkylamino, monohydroxy($C_1$–$C_4$)alkylamino, imidazolinium, and ammonium radicals.

Among the para-phenylenediamines of formula (XI) above, mention may be made of para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-N,N-bis(β-hydroxyethyl)-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,β-dihydroxypropyl)-para-phenylenediamine, N-(4'-aminophenyl)-para-phenylenediamine, N-phenyl-para-phenylenediamine and 2-β-hydroxyethyloxy-para-phenylenediamine, 2-β-acetylaminoethyloxy-para-phenylenediamine, N-(β-methoxyethyl)-para-phenylenediamine, 2-methyl-1-N-β-hydroxyethyl-para-phenylenediamine, and the acid addition salts thereof.

Among the para-phenylenediamines of formula (XI) above, para-phenylenediamine, para-toluenediamine, 2-isopropyl-para-phenylenediamine, 2hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, and 2-chloro-para-phenylenediamine, and the acid addition salts thereof may be mentioned.

(II) As used herein, the term double bases means compounds comprising at least two aromatic nuclei bearing at least one of amino and hydroxyl groups.

Among the double bases that can be used as oxidation bases in the dye compositions disclosed herein, mention may be made of the compounds corresponding to formula (X) below, and the acid addition salts thereof:

(X)

in which:

Z1 and Z2, which may be identical or different, are chosen from hydroxyl radicals and —NH₂ radicals which may be substituted with at least one $C_1$–$C_4$ alkyl radical or with a linker arm Y;

the linker arm Y is chosen from linear and branched alkylene chains having from 1 to 14 carbon atoms, which may be interrupted by or terminated with at least one nitrogenous group and at least one heteroatom such as oxygen, sulphur and nitrogen atoms, and optionally substituted with at least one of hydroxyl and $C_1$–$C_6$ alkoxy radicals;

R36 and R37 are chosen from a hydrogen atom, halogen atoms, $C_1$–$C_4$ alkyl radicals, $C_1$–$C_4$ monohydroxyalkyl radicals, $C_2$–$C_4$ polyhydroxyalkyl radicals, $C_1$–$C_4$ aminoalkyl radicals, and a linker arm Y;

R38, R39, R40, R41, R42, and R43, which may be identical or different, are chosen from a hydrogen atom, a linker arm Y, and $C_1$–$C_4$ alkyl radicals;

it being understood that the compounds of formula (X) have only one linker arm Y per molecule.

Among the nitrogenous groups of formula (X) above, mention maybe made of amino, mono($C_1$–$C_4$)alkylamino, di($C_1$–$C_4$)alkylamino, tri($C_1$–$C_4$)alkylamino, monohydroxy ($C_1$–$C_4$)alkylamino, imidazolinium, and ammonium radicals.

Among the double bases of formula (X) above, mention may be made of N,N'-bis-(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetra-methylenediamine, N,N'-bis(hydroxyethyl)-N,N'-bis-(4-aminophenyl)tetramethylenediamine, N,N'-bis(4-methyl-aminophenyl)tetramethylenediamine, N,N'-bis(ethyl)-N,N'-bis(4'-amino-3'-methylphenyl)ethylenediamine, 1,8-bis(2,5-diaminophenoxy)-3,5-dioxaoctane, and the acid addition salts thereof.

Among these double bases of formula (X), N,N'-bis(β-hydroxyethyl)-N,N'-bis(4'-aminophenyl)-1,3-diaminopropanol, 1,8-bis(2,5-diaminophenoxy)-3,5-dioxaoctane, and the acid addition salts thereof may be mentioned.

(III) the para-aminophenols corresponding to formula (XI) below, and the acid addition salts thereof:

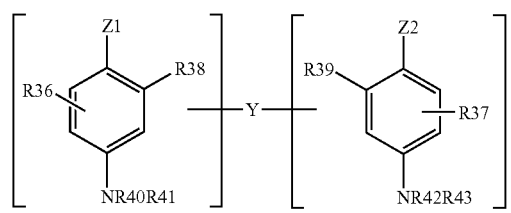

(XI)

in which:

R44 is chosen from a hydrogen atom, halogen atoms such as fluorine, $C_1$–$C_4$ alkyl radicals, $C_1$–$C_4$ monohydroxyalkyl radicals, ($C_1$–$C_4$)alkoxy($C_1$–$C_4$)alkyl radicals, $C_1$–$C_4$aminoalkyl radicals, and hydroxy($C_1$–$C_4$)alkylamino ($C_1$–$C_4$)alkyl radicals.

R45 is chosen from a hydrogen atom, halogen atoms such as fluorine, $C_1$–$C_4$ alkyl radicals, $C_1$–$C_4$ monohydroxyalkyl radicals, $C_2$–$C_4$ polyhydroxyalkyl radicals, $C_1$–$C_4$ aminoalkyl radicals, $C_1$–$C_4$ cyanoalkyl radicals, and ($C_1$–$C_4$) alkoxy-($C_1$–$C_4$)alkyl radicals.

R46 is chosen from a hydrogen atom and $C_1$–$C_4$ alkyl radicals.

Among the para-aminophenols of formula (XI) above, mention may be made of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, and the acid addition salts thereof.

(IV) the ortho-aminophenols that can be used as oxidation bases in the context of certain embodiments may be chosen from 2-aminophenol, 2-amino-1-hydroxy-5-methylbenzene, 2-amino-1-hydroxy-6-methylbenzene, 5-acetamido-2-aminophenol, and the acid addition salts thereof.

(V) among the heterocyclic bases that can be used as oxidation bases in the dye compositions in accordance with the present disclosure, mention may be made of pyridine derivatives, pyrimidine derivatives, pyrazole derivatives, and the acid addition salts thereof.

Among the pyridine derivatives, mention may be made of the compounds described, for example, in British patents GB 1 026 978 and GB 1 153 196, and compounds such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and the acid addition salts thereof.

Among the pyrimidine derivatives, mention may be made of the compounds described, for example, in German patent DE 2 359 399 or Japanese patents JP 88-169 571 and JP 91-10659 or patent application WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR-A-2 750 048 and among which mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol; 2-(7-aminopyrazolo[1,5-a]pyrimidin-3-ylamino)ethanol; 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol; 5,6-dimethylpyrazolo[1,5-a]pyrimidine-3,7-diamine; 2,6-dimethylpyrazolo[1,5-a]pyrimidine-3,7-diamine; 2,5,N7,N7-tetramethylpyrazolo[1,5-a]pyrimidine-3,7-diamine and 3-amino-5-methyl-7-imidazolylpropylamino-pyrazolo-[1,5-a]pyrimidine, the addition salts thereof and the tautomeric forms thereof, when a tautomeric equilibrium exists, and the acid addition salts thereof.

Among the pyrazole derivatives, mention may be made of the compounds described in patents DE 3 843 892, DE 4 133 957 and patent applications WO 94/08969, WO 94/08970, FR-A-2 733 749, and DE 195 43 988, such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-(β-hydroxyethyl)pyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropyl pyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the acid addition salts thereof.

According to certain embodiments, the oxidation bases may range from 0.0005% to 12% by weight relative to the total weight of the composition, for example from 0.005% to 8% by weight relative to the total weight of the composition.

The couplers that may be used in the dyeing method according to certain embodiments may be those conventionally used in oxidation dye compositions, that is to say meta-aminophenols, meta-phenylenediamines and meta-diphenols, naphthols and heterocyclic couplers such as, for example, indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles and quinolines, and the acid addition salts thereof.

These couplers may be chosen for example from 2,4-diamino-1-(β-hydroxyethyloxy)benzene, 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2-amino-3-hydroxypyridine, 3,6-dimethylpyrazolo[3,2-c]-1,2,4-triazole, 2,6-dimethylpyrazolo[1,5-b]-1,2,4-triazole, and the acid addition salts thereof.

When they are present, these couplers may represent from 0.0001% to 10% by weight relative to the total weight of the composition, such as from 0.005% to 5% by weight relative to the total weight of the composition.

In general, the acid addition salts of the oxidation bases and couplers may be chosen from hydrochlorides, hydrobromides, sulphates, tartrates, lactates, and acetates.

The composition as disclosed herein may also comprise direct dyes, in addition to the oxidation dyes defined above, in order to enrich the shades with glints. These direct dyes may be chosen from neutral, cationic and anionic nitro dyes, azo dyes and anthraquinone dyes, in a weight proportion ranging from 0.001% to 20%, such as from 0.01% to 10% of the total weight of the composition.

The composition (A) and/or the composition (B) may further comprise, for example, at least one cationic or amphoteric substantive polymer different from the associative polymers of disclosed herein.

As used herein, the term "cationic polymer" denotes any polymer comprising cationic groups and/or groups that may be ionized into cationic groups.

The cationic substantive polymers that may be used in accordance with the present disclosure may be chosen from all those already known per se as improving the cosmetic properties of the hair, for example those described in patent application EP A 337 354 and in French patents FR 2 270 846; 2 383 660; 2 598 611; 2 470 596; and 2 519 863.

The cationic polymers that may be used may be chosen from those comprising units comprising at least one of primary, secondary, tertiary and quaternary amine groups, which may either form part of the main polymer chain or may be derived from a side substituent attached directly thereto.

The cationic polymers used generally have a number-average molecular mass ranging from 500 to $5 \times 10^6$, such as from $10^3$ to $3 \times 10^6$.

Among the cationic polymers, those that may be mentioned by way of non-limiting example include polyamine, polyamino amide, and polyquaternary ammonium polymers.

These polymers are known products. They are described for example in French Patents Nos. 2 505 348 and 2 542 997. Among the said polymers, mention may be made of:

(1) homopolymers and copolymers derived from at least one of acrylic esters, acrylic amides, methacrylic esters, and methacrylic amides, and comprising at least one of the units of formula (XII), (XIII), (XIV) and (XV) below:

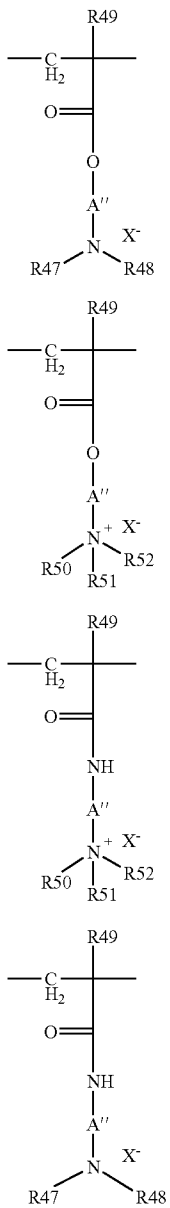

in which:

R49, which may be identical or different, is chosen from a hydrogen atom and a $CH_3$ radical;

A", which may be identical or different, is chosen from linear and branched alkyl groups having 1 to 6 carbon atoms, such as 2 or 3 carbon atoms, and hydroxyalkyl groups having 1 to 4 carbon atoms;

R50, R51, and R52, which may be identical or different, are chosen from alkyl groups having from 1 to 6 carbon atoms;

R47 and R48, which may be identical or different, are chosen from a hydrogen atom and alkyl groups having from 1 to 6 carbon atoms, such as methyl and ethyl;

X is chosen from anions derived from inorganic and organic acids, such as methosulphate anions and halides such as chloride and bromide.

The polymers of family (1) may also comprise at least one unit derived from comonomers which may be chosen from the family of acrylamides, methacrylamides, diacetone acrylamides, acrylamides, and methacrylamides substituted on the nitrogen with at least one of lower ($C_1$–$C_4$) alkyls, acrylic acids, acrylic esters, methacrylic acids, and methacrylic esters thereof, vinyliactams such as vinylpyrrolidone and vinylcaprolactam, and vinyl esters. Thus, among these polymers of family (1), mention may be made of:

copolymers of acrylamide and of dimethylaminoethyl methacrylate quaternized with dimethyl sulphate or with a dimethyl halide, such as the product sold under the name HERCOFLOC® by the company Hercules, the copolymers of acrylamide and of methacryloyloxyethyltrimethylammonium chloride described, for example, in patent application EP A 080 976 and sold under the name Bina Quat P 100 by the company Ciba Geigy, the copolymer of acrylamide and of methacryloyloxyethyltrimethylammonium methosulphate sold under the name RETEN® by the company Hercules, quaternized and non-quaternized vinylpyrrolidone/dialkylaminoalkyl acrylate and methacrylate copolymers, such as the products sold under the name GAFQUAT® by the company ISP, such as, for example, GAFQUAT® 734, and GAFQUAT® 755, and the products known as Copolymer 845, 958, and 937. These polymers are described in detail in French patents 2 077 143 and 2 393 573, dimethylaminoethyl methacrylate/vinylcaprolactam/vinylpyrrolidone terpolymers, such as the product sold under the name GAFFIX® VC 713 by the company ISP, vinylpyrrolidone/methacrylamidopropyldimethylamine copolymers sold in particular under the name STYLEZE® CC 10 by ISP, and quaternized vinylpyrrolidone/dimethylaminopropylmethacrylamide copolymers such as the product sold under the name GAFQUAT® HS 100 by the company ISP.

(2) The cellulose ether derivatives comprising quaternary ammonium groups, described in French patent 1 492 597, for example polymers sold under the names JR, such as JR 400, JR 125, and JR 30M, and LR, such as LR 400 and LR 30M, by the company Union Carbide Corporation. These polymers are also defined in the CTFA dictionary as quaternary ammoniums of hydroxyethylcellulose that have reacted with an epoxide substituted with a trimethylammonium group.

(3) Cationic cellulose derivatives such as cellulose copolymers and cellulose derivatives grafted with a water-soluble monomer of quaternary ammonium, and described for example in U.S. Pat. No. 4,131,576, such as hydroxyalkylcelluloses, for instance hydroxymethyl-, hydroxyethyl-, and hydroxypropylcelluloses grafted, for example, with at least one of methacryloylethyltrimethylammonium, methacrylamidopropyltrimethylammonium, and dimethyldiallylammonium salt.

The commercial products corresponding to this definition include, for example, the products sold under the names CELQUAT® L 200 and Celquat® H 100 by the company National Starch.

(4) The cationic polysaccharides described for example in U.S. Pat. Nos. 3,589,578 and 4,031,307, such as guar gums comprising cationic trialkylammonium groups. Guar gums modified with a salt, such as chloride of 2,3-epoxypropyltrimethylammonium may be used, for example.

Such products are sold for example under the trade names JAGUAR® C13 S, JAGUAR® C 15, JAGUAR® C 17, and JAGUAR® C 162 by the company Meyhall.

(5) Polymers comprising piperazinyl units and polymers of divalent alkylene and hydroxyalkylene radicals having straight and/or branched chains, optionally interrupted by at least one of oxygen atoms, sulphur atoms, nitrogen atoms, aromatic rings, and heterocyclic rings, as well as the oxidation and/or quaternization products of these polymers. Such polymers are described, for example, in French Patent Nos. 2 162 025 and 2 280 361.

(6) Water-soluble polyamino amides prepared for example by polycondensation of an acidic compound with a polyamine; these polyamino amides can be crosslinked with at least one of epihalohydrin, diepoxide, dianhydride, unsaturated dianhydride, bis-unsaturated derivatives, bis-halohydrin, bis-azetidinium, bis-haloacyldiamine, bis-alkyl halide, and oligomers resulting from the reaction of at least one difunctional compound which is reactive with at least one of bis-halohydrin, bis-azetidinium, bis-haloacyldiamine, bis-alkyl halide, epihalohydrin, diepoxide, and a bis-unsaturated derivative. The crosslinking agent may be used in proportions ranging from 0.025 to 0.35 mol per amine group of the polyamino amide. These polyamino amides can be alkylated or, if they comprise at least one tertiary amine functional group, they can be quaternized. Such polymers are described, for example, in French Patent Nos. 2 252 840 and 2 368 508.

(7) The polyamino amide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl radical has from 1 to 4 carbon atoms, and for example methyl, ethyl, and propyl. Such polymers are described, for example, in French Patent No. 1 583 363.

Among these derivatives, mention may be made of the adipic acid/dimethylaminohydroxypropyl/diethylenetriamine polymers sold under the name Cartaretine F, F4, and F8 by the company Sandoz.

(8) The polymers obtained by reaction of a polyalkylene polyamine comprising two primary amine groups and at least one secondary amine group with a dicarboxylic acid chosen from diglycolic acid and saturated aliphatic dicarboxylic acids having from 3 to 6 carbon atoms. The molar ratio between the polyalkylene polyamine and the dicarboxylic acid may range from 0.8:1 to 1.4:1. The polyamino amide resulting therefrom may be reacted with epichlorohydrin in a molar ratio of epichlorohydrin relative to the secondary amine group of the polyamino amide ranging from 0.5:1 to 1.8:1. Such polymers are described, for example, in U.S. Pat. Nos. 3,227,615 and 2,961,347.

Polymers of this type are sold for example under the name HERCOSETT® 57 by the company Hercules Inc. and under the name PD 170 or DELSETTE® 101 by the company Hercules in the case of the adipic acid/epoxypropyl/diethylenetriamine copolymer.

(9) Cyclopolymers of alkyldiallylamine and copolymers of dialkyldiallylammonium, such as the homopolymers and copolymers comprising, as the main constituent of the chain, units corresponding to formula (XVI) or (XVII):

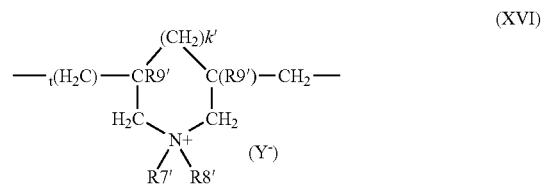

(XVI)

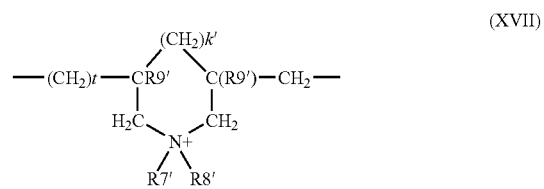

(XVII)

in which formulae k' and t are chosen from 0 and 1, the sum k'+t being equal to 1; R9' is chosen from a hydrogen atom and methyl radicals; R7' and R8', which may be identical or different, are chosen from alkyl groups having from 1 to 6 carbon atoms, hydroxyalkyl groups in which the alkyl group may have 1 to 5 carbon atoms, and lower $C_1$–$C_4$ amidoalkyl groups, or R7' and R8' can denote, together with the nitrogen atom to which they are attached, heterocyclic groups such as piperidyl and morpholinyl; R7' and R8', which may be identical or different, may denote an alkyl group having from 1 to 4 carbon atoms; $Y^-$ is an anion such as bromide, chloride, acetate, borate, citrate, tartrate, bisulphate, bisulphite, sulphate, and phosphate. These polymers are described for example in French Patent No. 2 080 759 and in its Certificate of Addition 2 190 406.

Among the polymers defined above, mention may be made of the dimethyldiallylammonium chloride homopolymer sold under the name MERQUAT® 100 by the company Calgon, and its homologues of low weight-average molecular mass, and the copolymers of diallyldimethylammonium chloride and of acrylamide, sold under the name MERQUAT® 550.

(10) The quaternary diammonium polymer comprising repeating units corresponding to the formula:

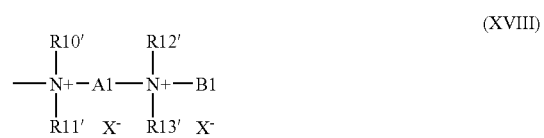

(XVIII)

in which formula (XVIII):

R10', R11', R12', and R13', which may be identical or different, are chosen from aliphatic, alicyclic, and arylaliphatic radicals having from 1 to 6 carbon, and lower hydroxyalkylaliphatic radicals, or alternatively R10', R11', R12', and R13', together or separately, constitute, with the nitrogen atoms to which they are attached, heterocycles optionally comprising a second heteroatom other than nitrogen, or alternatively R10', R11', R12', and R13' are chosen from linear and branched $C_1$–$C_6$ alkyl radicals substituted with at least one of nitrile groups, ester groups, acyl groups, amide groups, and groups —CO—O—R14'-D1 and —CO—NH—R14'-D1 where R14' is chosen from alkylene and D1 is a quaternary ammonium group;

A1 and B1 are chosen from linear and branched, saturated and unsaturated polymethylene groups having from 2 to 6 carbon atoms, and which may contain, linked to or intercalated in the main chain, at least one aromatic ring and at least one of an oxygen atom, a sulphur atom, and sulphoxide, sulphone, disulphide, amino, alkylamino, hydroxyl, quaternary ammonium, ureido, amide, and ester groups; and $X^-$ is chosen from anions derived from at least one acid chosen from inorganic acids and organic acids;

A1, R10' and R12' can form, together with the two nitrogen atoms to which they are attached, a piperazine ring. In addition, if A1 is a linear or branched, saturated or unsaturated alkylene or hydroxyalkylene radical, B1 can also be a group —$(CH_2)_n$—CO-D-OC—$(CH_2)_n$— in which n ranges from 1 to 100, such as from 1 to 50, and D is chosen from:

a) glycol residues of formula: —O-Z1-O—, where Z1 is chosen from linear and branched hydrocarbon-based radicals and groups corresponding to one of the following formulae:

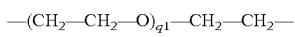

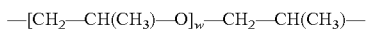

where q1 and w, which may be the same or different, are each an integer ranging from 1 to 4, representing a defined and unique degree of polymerization or any number from 1 to 4 representing an average degree of polymerization;

b) bis-secondary diamine residues such as piperazine derivatives;

c) bis-primary diamine residues of formula: —NH—Y3-NH—, where Y3 is chosen from linear and branched hydrocarbon-based radicals, and divalent radicals

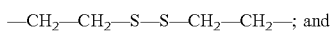

d) ureylene groups of formula: —NH—CO—NH—.

For example, $X^-$ is an anion such as chloride and bromide.

These polymers generally have a number-average molecular mass ranging from 1,000 to 100,000.

Polymers of this type are described for example in French Patent Nos. 2 320 330; 2 270 846; 2 316 271; 2 336 434; and 2 413 907 and U.S. Pat. Nos. 2,273,780; 2,375,853; 2,388, 614; 2,454,547; 3,206,462; 2,261,002; 2,271,378; 3,874, 870; 4,001,432; 3,929,990; 3,966,904; 4,005,193; 4,025, 617; 4,025,627; 4,025,653; 4,026,945; and 4,027,020.

It is also possible to use polymers that comprise repeating units corresponding to the following formula (XIX):

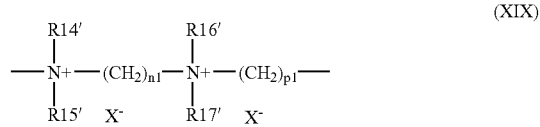

in which R14', R15', R16', and R17', which may be identical or different, are chosen from alkyl radicals and hydroxyalkyl radicals having from 1 to 4 carbon atoms, n1 and p1 are integers ranging from 2 to 20, and $X^-$ is an anion derived from an inorganic or organic acid.

(11) Polyquaternary ammonium polymers comprising repeating units of formula (XX):

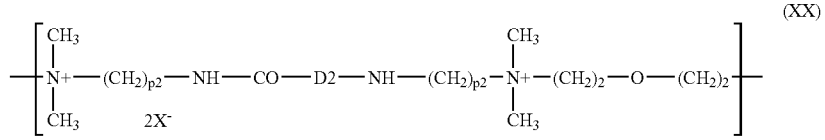

in which:

p2 is chosen from integers ranging from 1 to 6,

D2 is chosen from zero (i.e., a direct bond) and groups —$(CH_2)_{r3}$—CO— in which r3 is chosen from 4 and 7, and $X^-$ is an anion derived from an organic or inorganic acid.

The cationic polymers comprising units of formula (XX) are described for example in patent application EP A 122 324 and can be prepared by the processes described in U.S. Pat. Nos. 4,157,388; 4,390,689; 4,702,906; and 4,719,282.

Among these polymers, mention may be made of those having a molecular mass, measured by carbon 13 NMR, of less than 100,000, and in whose formula p2 is 3; and a) D2 represents a group —$(CH_2)_4$—CO—, $X^-$ denotes a chlorine atom, the molecular mass measured by carbon 13 NMR ($^{13}$C NMR) being about 5,600; a polymer of this type is sold by the company Miranol under the name MIRAPOL®-AD1, b) D2 represents a group —$(CH_2)_7$CO—, $X^-$ is a chlorine atom, the molecular mass measured by carbon 13 NMR ($^{13}$C NMR) being about 8,100; a polymer of this type is sold by the company Miranol under the name MIRAPOL®-AZ1, c) D2 is zero (i.e., a direct bond), $X^-$ is a chlorine atom, the molecular mass measured by carbon 13 NMR ($^{13}$C NMR) being about 25,500; a polymer of this type is sold by the company Miranol under the name MIRAPOL®-A15, or d) a block copolymer comprising units corresponding to the polymers described in paragraphs a) and c), sold by the company Miranol under the names MIRAPOL®-9, having a $^{13}$C NMR molecular mass of about 7,800, MIRAPOL®-175, having a $^{13}$C NMR molecular mass about 8,000, and MIRAPOL®-95, having a $^{13}$C NMR molecular mass about 12,500.

For example, in accordance with certain embodiments, to the polymer with units of formula (XX) in which p2 is 3, D2 is zero, and X⁻ denotes a chlorine atom, the molecular mass measured by carbon 13 NMR ($^{13}$C NMR) being about 25,500.

(12) Quaternary polymers of vinylpyrrolidone and of vinylimidazole, such as, for example, the products sold under the names LUVIQUAT® FC 905, FC 550, and FC 370 by the company BASF.

(13) Polyamines such as POLYQUART® H sold by Henkel, which is referred to as polyethylene glycol (15) tallow polyamine in the CTFA dictionary.

(14) Crosslinked methacryloyloxy($C_1$–$C_4$)alkyltri ($C_1$–$C_4$)alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound comprising olefinic unsaturation, such as methylenebisacrylamide. A crosslinked acrylamide/methacryloyloxyethyltrimethylammonium chloride copolymer, comprising 20% and 80%, respectively, by weight, in the form of a dispersion comprising 50% by weight of the said copolymer in mineral oil can be used for example. This dispersion is sold under the name SALCARE® SC 92 by the company Allied Colloids. A crosslinked methacryloyloxyethyltrimethylammonium chloride homopolymer comprising about 50% by weight of the homopolymer in mineral oil or in a liquid ester can also be used. These dispersions are sold under the names SALCARE® SC 95 and SALCARE®. SC 96 by the company Allied Colloids.

Other cationic polymers which can be used in the context of present disclosure include polyalkyleneimines, such as polyethyleneimines, polymers comprising vinylpyridine, polymers comprising vinylpyridinium units, condensates of polyamines and of epichlorohydrin, quaternary polyureylenes, and chitin derivatives.

Among all the cationic polymers which may be used in the context of the composition disclosed herein, mention may be made of the use the polymers of families (1), (9), (10), (11), (12), and (14), such as the polymers comprising repeating units of formulae (W) and (U) below:

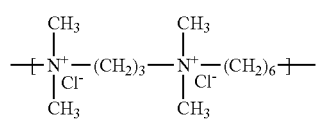

(W)

and for example those whose molecular weight, determined by gel permeation chromatography, ranges from 9,500 to 9,900;

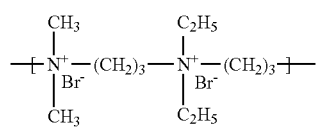

(U)

and for example those whose molecular weight, determined by gel permeation chromatography, is about 1,200.

The concentration of substantive cationic polymer in the composition according to certain embodiments may range from 0.01% to 10% by weight relative to the total weight of the composition, such as from 0.05% to 5% or from 0.1% to 3%.

Amphoteric Polymers

The amphoteric substantive polymers that may be used in accordance with the present disclosure may be chosen from polymers comprising units K and M randomly distributed in the polymer chain, in which K denotes a unit derived from a monomer comprising at least one basic nitrogen atom and M denotes a unit derived from an acidic monomer comprising at least one of carboxylic groups and sulphonic groups, or alternatively K and M may denote groups derived from zwitterionic carboxybetaine or sulphobetaine monomers;

K and M may also denote a cationic polymer chain comprising at least one of primary, secondary, tertiary, and quaternary amine groups, in which at least one of the amine groups bears a carboxylic or sulphonic group linked via a hydrocarbon-based radical, or alternatively K and M form part of a chain of a polymer comprising an α,β-dicarboxylic ethylene unit in which one of the carboxylic groups has been made to react with a polyamine comprising at least one of primary and secondary amine groups.

The amphoteric polymers corresponding to the above definition that may be mentioned are chosen from the following polymers:

(1) polymers resulting from the copolymerization of a monomer derived from a vinyl compound bearing a carboxylic group such as acrylic acid, methacrylic acid, maleic acid, α-chloroacrylic acid, and a monomer derived from a substituted vinyl compound comprising at least one basic atom, such as dialkylaminoalkyl methacrylate and acrylate, dialkylaminoalkylmethacrylamide and -acrylamide. Such compounds are described, for example, in U.S. Pat. No. 3,836,537. Mention may also be made of the sodium acrylate/acrylamidopropyltrimethylammonium chloride copolymer sold under the name POLYQUART® KE 3033 by the company Henkel.

The substituted vinyl compound comprising at least one basic atom may also be a dialkyldiallylammonium, salt such as dimethyldiallylammonium chloride. The copolymers of acrylic acid and of the latter monomer are sold under the names MERQUAT® 280, MERQUAT® 295, and MERQUAT® Plus 3330 by the company Calgon.

(2) Polymers comprising units derived from:
a) at least one monomer chosen from acrylamides and methacrylamides substituted on the nitrogen with an alkyl radical,
b) at least one acidic comonomer comprising at least one reactive carboxylic group, and
c) at least one basic comonomer such as esters comprising primary, secondary, tertiary, and quaternary amine substituents of acrylic and methacrylic acids and the product of quaternization of dimethylaminoethyl methacrylate with dimethyl or diethyl sulphate.

The N-substituted acrylamides or methacrylamides which may be, for example, groups in which the alkyl radicals have from 2 to 6 carbon atoms, such as N-ethylacrylamide, N-tert-butylacrylamide, and the corresponding methacrylamides.

The acidic comonomers may be chosen, for example, from acrylic acid, methacrylic acid, crotonic acid, itaconic acid, maleic acid and fumaric acid and alkyl monoesters, having 1 to 4 carbon atoms, of maleic acids, maleic anhydrides, fumaric acids, and fumaric anhydrides.

Basic comonomers according to certain embodiments of the present disclosure include aminoethyl, butylaminoethyl, N,N'-dimethylaminoethyl, and N-tert-butylaminoethyl methacrylates.

The copolymers whose CTFA (4th edition, 1991) name is octylacrylamide/acrylates/butylaminoethyl methacrylate copolymer such as the products sold under the name AMPHOMER® or LOVOCRYL® 47 by the company National Starch may be used.

(3) Crosslinked and alkylated polyamino amides partially or totally derived from polyamino amides of general formula:

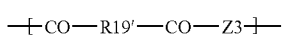
(XXI)

in which R19' is chosen from divalent radicals derived from saturated dicarboxylic acids, mono- or dicarboxylic aliphatic acid comprising at least one ethylenic double bond, esters of a lower alkanol having 1 to 6 carbon atoms with these acids, and radicals derived from the addition of any one of the said acids to a bis(primary) or bis(secondary) amine, and Z3 is chosen from bis(primary) radicals and mono- or bis(secondary) polyalkylene-polyamine radicals and for example, may represent:

a) in proportions ranging from 60 to 100 mol %, the radical

(XXII)

where x' is 2 and p3 is chosen from 2 and 3, or alternatively where x' is 3 and p3 is 2, this radical being derived from a compound chosen from diethylenetriamine, triethylenetetraamine, and dipropylenetriamine;

b) in proportions ranging from 0 to 40 mol %, the radical (X)(II) above in which x' is 2 and p3 is 1 and which is derived from ethylenediamine, or the radical deriving from piperazine:

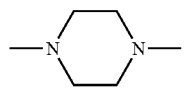

c) in proportions ranging from 0 to 20 mol %, the —NH—(CH$_2$)$_6$—NH— radical derived from hexamethylenediamine, these polyamino amines being crosslinked by addition of a difunctional crosslinking agent chosen from epihalohydrins, diepoxides, dianhydrides, and bis-unsaturated derivatives, using from 0.025 to 0.35 mol of crosslinking agent per amine group of the polyamino amide and alkylated by the action of at least one of acrylic acid, chloroacetic acid, alkane sultones, and salts thereof.

The saturated carboxylic acids may be chosen from acids having 6 to 10 carbon atoms, such as adipic acid, 2,2,4-trimethyladipic acid, 2,4,4-trimethyladipic acid, terephthalic acid and acids comprising at least one ethylenic double bond such as, for example, acrylic acid, methacrylic acid, and itaconic acid.

The alkane sultones used in the alkylation may be chosen from propane sultone and butane sultone, and the salts of the alkylating agents may be chosen from sodium and potassium salts.

(4) Polymers comprising zwitterionic units of formula:

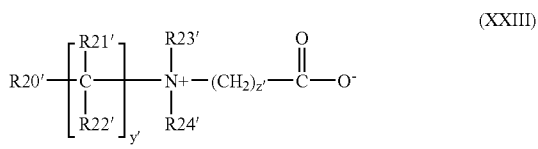
(XXIII)

in which R20' denotes a polymerizable unsaturated group such as acrylate, methacrylate, acrylamide, and methacrylamide groups, y' and z' represent an integer from 1 to 3, R21' and R22' are chosen from hydrogen atoms, methyls, ethyls, and propyls, R23' and R24' are chosen from a hydrogen atom and alkyl radicals such that the sum of the carbon atoms in R23' and R24' does not exceed 10.

The polymers comprising such units may also comprise units derived from non-zwitterionic monomers such as dimethyl acrylate, diethylaminoethyl acrylate, methacrylate, alkyl acrylates, methacrylates, acrylamides, methacryiamides, and vinyl acetate.

By way of example, mention may be made of the copolymer of butyl methacrylate/dimethylcarboxymethylammonioethyl methacrylate such as the product sold under the name Diaformer Z301 by the company Sandoz.

(5) Polymers derived from chitosan, described for example in French Patent No. 2 137 684 or U.S. Pat. No. 3,879,376, comprising together in their chain monomer units corresponding to formulae (XXIV), (XXV) and (XXVI) below:

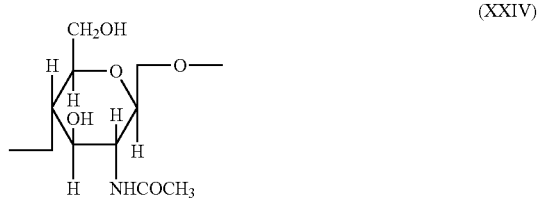
(XXIV)

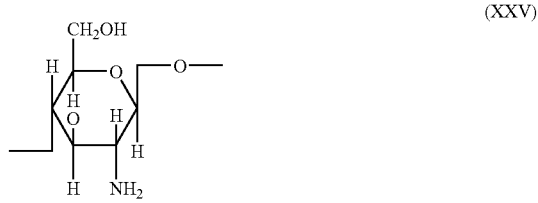
(XXV)

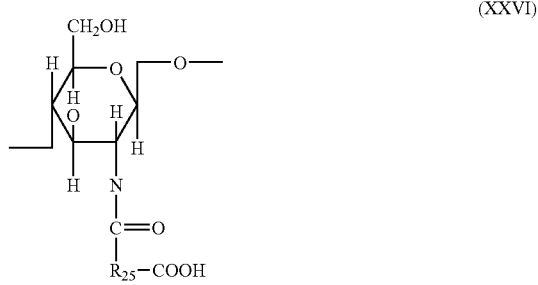
(XXVI)

the unit (XXIV) being present in proportions ranging from 0 to 30%, the unit (XXV) in proportions ranging from 5 to 50%, and the unit (XXVI) in proportions ranging from 30 to 90%, it being understood that, in this unit (XXVI), $R_{25}$ represents a radical of formula:

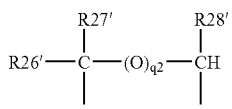

in which q2 is chosen from zero and 1;

if q2 is 0, R26', R27', and R28', which may be identical or different, are chosen from a hydrogen atom, methyl residues, hydroxyl residues, acetoxy residues, amino residues, monoalkylamine residues, and dialkylamine residues which are optionally interrupted by at least one nitrogen atom and optionally substituted with at least one of amine, hydroxyl, carboxyl, alkylthio, and sulphonic groups, alkylthio residues in which the alkyl groups bear amino residues, at least one of the radicals R26', R27', and R28' being, in this case, a hydrogen atom;

or, if q2 is 1, R26', R27', and R28' represent a hydrogen atom, as well as the salts formed by these compounds with bases or acids.

According to certain embodiments, polymers of this type may comprise from 0% to 20% by weight of units (XXIV), from 40% to 50% by weight of units (XXV) and from 40% to 50% by weight of units (XXVI) in which R25' denotes the radical —CH$_2$—CH$_2$—.

(6) Polymers derived from the N-carboxyalkylation of chitosan, such as N-carboxymethylchitosan and N-carboxybutylchitosan sold under the name Evalsan by the company Jan Dekker.

(7) Polymers corresponding to the general formula (XXVII) as described, for example, in French Patent No. 1 400 366:

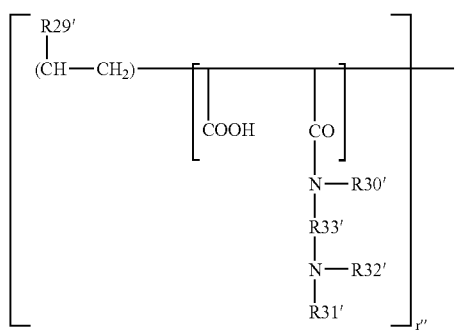

(XXVII)

in which R29' is chosen from a hydrogen atom, CH$_3$O, CH$_3$CH$_2$O, and phenyl radicals, R30' is chosen from a hydrogen atom and lower alkyl radicals such as methyl and ethyl, R31' is chosen from a hydrogen atom and lower alkyl radicals such as methyl and ethyl, R32' is chosen from lower alkyl radicals such as methyl and ethyl, and radicals corresponding to the formula: —R33'-N(R31')$_2$, and R33' is chosen from —CH$_2$—CH$_2$—, —CH$_2$—CH$_2$—CH$_2$—, and —CH$_2$—CH(CH$_3$)— groups, R31' having the meanings mentioned above, as well as the higher homologues of these radicals, comprising up to 6 carbon atoms, r'' is such that the molecular weight ranges from 500 to 6,000,000, such as from 1,000 to 1,000,000.

(8) Amphoteric polymers of the type -D1-X1-D1-X1- chosen from:

a) polymers obtained by the action of chloroacetic acid or sodium chloroacetate on compounds containing at least one unit of formula:

-D1-X1-D1-X1-D1-     (XXVIII)

where D1 denotes a radical

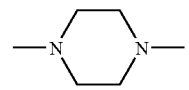

and X1 is chosen from the symbols E and E', E and E', which may be identical or different, denote a divalent radical which is an alkylene radical with a straight or branched chain having up to 7 carbon atoms in the main chain, which is unsubstituted or substituted with hydroxyl groups and which can comprise, in addition to the oxygen, nitrogen, and sulphur atoms, 1 to 3 aromatic and/or heterocyclic rings; the oxygen, nitrogen, and sulphur atoms being present in the form of at least one of ether, thioether, sulphoxide, sulphone, sulphonium, alkylamine, alkenylamine, hydroxyl, benzylamine, amine oxide, quaternary ammonium, amide, imide, alcohol, ester and urethane groups;

b) polymers of formula:

-D1-X1-D1-X1-     (XXIX)

where D1 denotes a radical

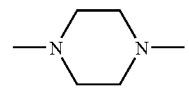

and X1 is chosen from the symbols E and E'' and is at least once E''; E having the meaning given above and E'' being a divalent radical which is an alkylene radical with a straight or branched chain having up to 7 carbon atoms in the main chain, which is unsubstituted or substituted with at least one hydroxyl radical and comprising at least one nitrogen atom, the nitrogen atom being substituted with an alkyl chain which is optionally interrupted by an oxygen atom and necessarily comprising at least one carboxyl functional group or at least one hydroxyl functional group and betainized by reaction with at least one of chloroacetic acid and sodium chloroacetate.

(9) (C$_1$–C$_5$)alkyl vinyl ether/maleic anhydride copolymers partially modified by semiamidation with an N,N-dialkylaminoalkylamine such as N,N-dimethylaminopropylamine or by semiesterification with an N,N-dialkanolamine. These copolymers can also comprise other vinyl comonomers such as vinylcaprolactam.

The amphoteric polymers that may be used according to certain embodiments are those of family (1).

As disclosed herein, the amphoteric substantive polymers may be present in an amount ranging from 0.01% to 10% by weight, such as from 0.05% to 5% by weight or from 0.1% to 3% by weight relative to the total weight of the composition.

The compositions disclosed herein may include at least one surfactant.

The at least one surfactant may be chosen arbitrarily, alone or as mixtures, from anionic, amphoteric, non-ionic, zwitterionic and cationic surfactants.

The at least one surfactant which may be suitable for the implementation of certain embodiments may be the following:

(i) Anionic Surfactants:

As examples of anionic surfactants which may be used, alone or as mixtures, in the context of certain embodiments disclosed herein, mention may be made of salts, in particular alkali metal salts, such as sodium salts, ammonium salts, amine salts, amino alcohol salts, and magnesium salts of the following compounds: alkyl sulphates, alkyl ether sulphates, alkylamido ether sulphates, alkylaryl polyether sulphates, monoglyceride sulphates; alkylsulphonates, alkyl phosphates, alkylamidesulphonates, alkylarylsulphonates, α-olefinsulphonates, paraffinsulphonates; ($C_6$–$C_{24}$)alkyl sulphosuccinates, ($C_6$–$C_{24}$)alkyl ether sulphosuccinates, ($C_6$–$C_{24}$) alkylamide sulphosuccinates; ($C_6$–$C_{24}$)alkyl sulphoacetates; ($C_6$–$C_{24}$)acyl sarcosinates, and ($C_6$–$C_{24}$)acyl glutamates. It is also possible to use the carboxylic esters of ($C_6$–$C_{24}$)alkyl polyglycosides, such as alkylglucoside citrates, alkylpolyglycoside tartrates, and alkylpolyglycoside sulphosuccinates, alkylsulphosuccinamates; acyl isethionates and N-acyltaurates, the alkyl and acyl radicals of all of these various compounds having, for example, from 12 to 20 carbon atoms, and the aryl radicals denoting, for example at least one of phenyl groups and benzyl groups. Among the anionic surfactants which can also be used, mention may also be made of fatty acid salts such as the salts of oleic, ricinoleic, palmitic, and stearic acids, coconut oil acid and hydrogenated coconut oil acid; and acyl lactylates in which the acyl radical has 8 to 20 carbon atoms. Alkyl-D-galactosideuronic acids and their salts, polyoxyalkylenated ($C_6$–$C_{24}$)alkyl ether carboxylic acids, polyoxyalkylenated ($C_6$–$C_{24}$)alkyl aryl ether carboxylic acids, polyoxyalkylenated ($C_6$–$C_{24}$) alkylamido ether carboxylic acids and their salts, such as those having from 2 to 50 alkylene oxide, such as ethylene oxide, groups, and mixtures thereof can also be used.

(ii) Non-Ionic Surfactants:

The non-ionic surfactants are also compounds that are well known per se. See for example in this respect "Handbook of Surfactants" by M. R. Porter, published by. Blackie & Son (Glasgow and London), 1991, pp. 116–178. As disclosed herein, the non-ionic surfactants are optional in certain embodiments. Thus, they may be selected from, for example, polyethoxylated alkylphenols, polypropoxylated alkylphenols, alpha-diols and alcohols having a fatty chain having, for example, 8 to 18 carbon atoms, it being possible for the number of ethylene oxide or propylene oxide groups to range from 2 to 50. Mention may also be made of copolymers of ethylene oxide and of propylene oxide, condensates of ethylene oxide and of propylene oxide with fatty alcohols; polyethoxylated fatty amides having for example from 2 to 30 mol of ethylene oxide, polyglycerolated fatty amides having on average 1 to 5, such as 1.5 to 4, glycerol groups; alkyl polyglycosides, N-alkylglucamine derivatives, amine oxides such as ($C_{10}$–$C_{14}$)alkylamine oxides and N-acylaminopropylmorpholine oxides. It will be noted that alkyl polyglycosides constitute non-ionic surfactants that may be used in the context of certain embodiments.

(iii) Amphoteric and Zwitterionic Surfactants:

The amphoteric and zwitterionic surfactants, which are optional in certain embodiments, can be, for example, aliphatic secondary and tertiary amine derivatives in which the aliphatic radical is a linear or branched chain having 8 to 18 carbon atoms and comprising at least one water-solubilizing anionic group, for example carboxylate, sulphonate, sulphate, phosphate, and phosphonate. Mention may also be made of ($C_8$–$C_{20}$)alkylbetaines, sulphobetaines, ($C_8$–$C_{20}$) alkylamido($C_1$–$C_6$)alkylbetaines, and ($C_8$–$C_{20}$)alkylamido ($C_1$–$C_6$)alkylsulphobetaines.

Among the amine derivatives, mention may be made of the products sold under the name MIRANOL®, as described in U.S. Pat. Nos. 2,528,378 and 2,781,354 and classified in the CTFA dictionary, 3rd edition, 1982, under the names Amphocarboxyglycinates and Amphocarboxypropionates, of respective structures:

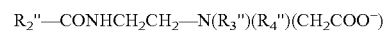

in which: $R_2''$ is chosen from linear and branched ($C_5$–$C_{20}$) alkyl radicals of, for example, an acid $R_2''$—COOH present in hydrolysed coconut oil, heptyl radicals, nonyl radicals, and undecyl radicals, $R_3''$ denotes a beta-hydroxyethyl group, and $R_4''$ denotes a carboxymethyl group;

and

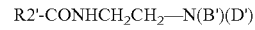

in which:
B' represents —$CH_2CH_2OV$, D' represents —$(CH_2)_{z''}$—Y''', wherein z'' is chosen from 1 and 2,
V is chosen from —$CH_2CH_2$—COOH groups and a hydrogen atom,
Y''' is chosen from —COOH radicals and —$CH_2$—CHOH—$SO_3H$ radicals,
R2' is chosen from linear and branched, saturated and unsaturated, ($C_5$–$C_{20}$) alkyl radicals of an acid R9'-COOH present, for example, in coconut oil or in hydrolysed linseed oil, alkyl radicals, such as $C_7$, $C_9$, $C_{11}$, and $C_{13}$ alkyl radicals, $C_{17}$ alkyl radicals and its iso form, and unsaturated $C_{17}$ radicals.

These compounds are classified in the CTFA dictionary, 5th edition, 1993, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphodipropionate, Disodium Caprylamphodipropionate, Disodium Capryloamphodipropionate, Lauroamphodipropionic acid, and Cocoamphodipropionic acid.

By way of example, mention may be made of the cocoamphodiacetate sold under the trade name MIRANOL® C2M concentrate by the company Rhodia Chimie.

(iv) Cationic Surfactants:

Among the cationic surfactants, mention may be made, for example, of: primary, secondary, and tertiary fatty amine salts, optionally polyoxyalkylenated; quaternary ammonium salts such as tetraalkylammonium, alkylamidoalkyltrialkylammonium, trialkylbenzylammonium, trialkylhydroxyalkylammonium, and alkylpyridinium chlorides and bromides; imidazoline derivatives; and cationic amine oxides.

The amounts of surfactants present in the composition disclosed herein may range from 0.01% to 40%, for example from 0.5% to 30% of the total weight of the composition.

The compositions disclosed herein may further comprise at least one non-associative rheology modifier such as cellulosic thickeners, for example hydroxyethylcellulose, hydroxypropylcellulose, and carboxymethylcellulose, etc., guar gum and its derivatives, for example hydroxypropylguar, etc., gums of microbial origin, for example xanthan gum and scleroglucan gum, etc., and synthetic thickeners such as crosslinked homopolymers of acrylic acid and of acrylamidopropanesulphonic acid.

The supplementary thickener may be present in an amount ranging from 0.01% to 10% by weight relative to the total weight of the composition.

The medium of the composition, which is suitable for dyeing, may be an aqueous medium comprising water and may advantageously comprise at least one cosmetically acceptable organic solvent including, for example, alcohols such as ethyl alcohol, isopropyl alcohol, benzyl alcohol, and phenylethyl alcohol, polyols and polyol ethers such as, for example, ethylene glycol monomethyl, monoethyl, and monobutyl ether, propylene glycol, and its ethers such as, for example, propylene glycol monomethyl ether, butylene glycol, dipropylene glycol, and also diethylene glycol alkyl ethers such as, for example, diethylene glycol monoethyl ether, and monobutyl ether.

The at least one solvent may then be present in amounts ranging from 0.5% to 20%, for example from 2% to 10% by weight, relative to the total weight of the composition.

The composition (A) may also comprise an effective amount of at least one additional agent, known previously elsewhere in oxidation dyeing, such as various common adjuvants, for instance sequestrants such as EDTA and etidronic acid, UV screening agents, waxes, volatile or non-volatile, cyclic, linear, or branched silicones, which are optionally organically modified, such as with amine groups, preservatives, ceramides, pseudoceramides, vegetable, mineral oils, synthetic oils, vitamins, and provitamins, for instance panthenol.

The said composition may also comprise at least one of reducing agents and antioxidants. These agents may be chosen for example from sodium sulphite, thioglycolic acid, thiolactic acid, sodium bisulphite, dehydroascorbic acid, hydroquinone, 2-methylhydroquinone, tert-butylhydroquinone, and homogentisic acid, and, in this case, they may generally be present in amounts ranging from 0.05% to 1.5% by weight relative to the total weight of the composition.

Needless to say, a person skilled in the art will take care to select the optional additional compound(s) mentioned above such that the advantageous properties intrinsically associated with the dye composition disclosed herein are not, or are not substantially, adversely affected by the envisaged addition(s).

In the ready-to-use composition and in the composition (B), the oxidizing agent may be chosen from urea peroxide, alkali metal bromates or ferricyanides, and persalts such as perborates and persulphates. For example, hydrogen peroxide may be used. This oxidizing agent may comprise an aqueous hydrogen peroxide solution whose titre may range, for example, from 1 to 40 volumes, such as from 5 to 40 volumes.

Oxidizing agents that may also be used include at least one redox enzyme such as laccases, peroxidases, and 2-electron oxidoreductases, for example uricase, where appropriate in the presence of their respective donor or co-factor.

The pH of the ready-to-use composition applied to the keratin fibers, i.e., the composition resulting from mixing together the dye composition (A) and the oxidizing composition (B), generally ranges from 4 to 11. It may range, for example, from 6 to 10 and may be adjusted to the desired value using acidifying or basifying agents that are well known in the art of dyeing of keratin fibers.

Among the basifying agents which may be mentioned, for example, are aqueous ammonia, alkali metal carbonates, alkanolamines such as monoethanolamine, diethanolamine, and triethanolamine and derivatives thereof, oxyethylenated and oxypropylenated hydroxyalkylamines and ethylenediamines, sodium hydroxide, potassium hydroxide, and the compounds of the following formula (XIX):

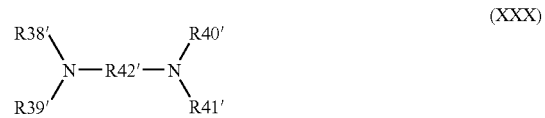

(XXX)

in which R42' is a propylene residue optionally substituted by at least one of a hydroxyl group and $C_1$–$C_4$ alkyl radicals; R38', R39', R40' and R41', which may be identical or different, are chosen from a hydrogen atom, $C_1$–$C_4$ alkyl radicals, and $C_1$–$C_4$ hydroxyalkyl radicals.

The acidifying agents may be chosen from those including, for example, mineral acids and organic acids, for instance hydrochloric acid, orthophosphoric acid, carboxylic acids, for instance tartaric acid, citric acid, lactic acid, and sulphonic acids.

The dyeing process as disclosed herein comprises applying the ready-to-use composition, prepared at the time of use from the compositions (A) and (B) described above, to wet or damp keratin fibers, and in leaving the composition to act for a waiting time ranging from 1 to 60 minutes, for example from 10 to 45 minutes, in rinsing the fibers and then in optionally washing the fibers with shampoo, then rinsing the fibers again and drying them.

One variant of this process comprises applying an above-described composition and a composition comprising an oxidizing agent sequentially with a time delay or simultaneously to wet or damp keratin fibers, with an optional intermediate rinse, and in leaving the said compositions to act for an exposure time ranging from 1 to 60 minutes and then in rinsing the fibers, and then optionally in washing the fibers with shampoo, then rinsing the fibers again and drying them.

The example which follows is intended to illustrate one embodiment.

The following composition was prepared (amounts given in percentages by weight):

| | |
|---|---|
| Oxyethylenated (2EO) stearyl alcohol | 4 |
| Oxyethylenated (21EO) stearyl alcohol | 3 |
| Cetylstearyl alcohol | 1 |
| Myristyl/cetyl/stearyl myristate/palmitate/stearate mixture (product sold under the name SPERMWAX ® VEGETAL by the company Robeco) | 1 |
| Sodium cetearyl sulphate | 1.5 |
| Fatty-chain cationic polyurethane obtained by condensing 1,3-bis(isocyanatomethylcyclohexane), N,N-dimethylethanolamine quaternized with bromododecane, N,N-dimethylethanolamine, and polyoxyethylene having a molecular weight of 10,000 | 1.5 |
| Alkoyl C12 glycerol ether (1.5 mol) | 2 |
| Merquat 100 in 40% strength aqueous solution | 4 |
| Titanium oxide | 0.15 |
| Sodium metabisulphite | 0.71 |
| EDTA (ethylenediaminetetraacetic acid) | 0.2 |
| Tert-butylhydroquinone | 0.3 |
| 1,4-diaminobenzene | 0.2 |
| Para-aminophenol | 1.2 |
| 1,3-dihydroxybenzene | 0.1 |

-continued

| | |
|---|---|
| 1-hydroxy-3-aminobenzene | 0.2 |
| 1-methyl-2-hydroxy-4-β-hydroxyethylaminobenzene | 0.8 |
| Monoethanolamine | 1 |
| Aqueous ammonia containing 20% NH$_3$ | 11 |
| Perfume q.s. | |
| Demineralized water q.s. | 100 |

This composition was mixed at the time of use with an oxidizing composition in the form of an emulsion comprising as an oxidizing agent 7.5% of hydrogen peroxide, in a proportion of 1 part by weight of dye composition per 1.5 parts by weight of oxidizing composition. The resulting mixture was applied to locks of natural hair having 90% white hairs and was left to act for 30 minutes. After rinsing, washing with shampoo and drying, hair was obtained which was dyed in a sustained coppery red light chestnut shade.

What is claimed is:
1. A composition for the oxidation dyeing of keratin fibers, comprising, in a medium suitable for dyeing,
   a) at least one oxidation dye;
   b) at least one fatty alcohol;
   c) at least one associative polymer chosen from cationic polyurethanes; and
   d) at least one compound chosen from fatty acid esters and metal oxides,
   wherein the ratio by weight of the at least one compound chosen from fatty acid esters and metal oxides to the at least one associative polymer ranges from 0.1 to 10.
2. The composition according to claim 1, wherein the keratin fibers are human keratin fibers.
3. The composition according to claim 2, wherein the human keratin fibers are hair.
4. The composition according to claim 1, wherein the at least one fatty acid ester is chosen from monoesters, diesters, and triesters obtained from the reaction of at least one acid chosen from linear and branched, saturated and unsaturated monoacids and linear and branched, saturated and unsaturated diacids having 8 to 30 carbon atoms with at least one alcohol chosen from saturated and unsaturated, linear, branched and cyclic monoalcohols and saturated and unsaturated, linear, branched and cyclic polyols having 2 to 100 carbon atoms and I to 30 hydroxyl groups.
5. The composition according to claim 4, wherein the at least one acid is chosen from stearic acid, palmitic acid, lauric acid, oleic acid, and myristic acid.
6. The composition according to claim 4, wherein the at least one alcohol is chosen from ethanol, isopropanol, isooctanol, dodecanol, stearyl alcohol, ethylene glycol, propylene glycol, glycerol, polyethylene glycols, polypropylene glycols, glucose, methyl glucose, sorbitol, sorbitol anhydride, and pentaerythritol.
7. The composition according to claim 4, wherein the monoalcohols or polyols are oxyalkylenated.
8. The composition according to claim 4, wherein the monoalcohols or polyols are oxyethylenated.
9. The composition according to claim 1, wherein the fatty acid ester is chosen from isopropyl myristate, stearyl stearate, ethylene glycol monostearate, ethylene glycol distearate, polyethylene glycol monostearate, polyethylene glycol distearate, sorbitan monopalmitate, glyceryl isostearate, propylene glycol dipelargonate, 2-ethylhexyl palmitate, sorbitan tristearate, di(2-ethylhexyl) sebacate, and glyceryl trihydroxystearate.

10. The composition according to claim 1, wherein the metal oxide is chosen from aluminium oxides, zinc oxides, magnesium oxides, and titanium oxides.
11. The composition according to claim 10, wherein the metal oxide is chosen from titanium oxides and mica-titanium oxide hybrid compounds.
12. The composition according to claim 11, wherein the titanium oxide is coated.
13. The composition according to claim 11, wherein the titanium oxide is uncoated.
14. The composition according to claim 1, wherein the at least one compound chosen from fatty acid esters and metal oxides is present in the composition in an amount ranging from 0.2% to 10% by weight, relative to the total weight of the composition.
15. The composition according to claim 14, wherein the at least one compound chosen from fatty acid esters and metal oxides is present in the composition in an amount ranging from 0.5% to 5% by weight, relative to the total weight of the composition.
16. The composition according to claim 1, wherein the at least one associative polymer is a cationic amphiphilic polyurethane of formula (Ia) below:

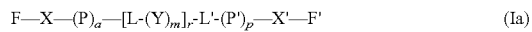

(Ia)

in which:
F and F', which may be identical or different, are chosen from hydrophobic groups and a hydrogen atom;
X and X', which may be identical or different, are chosen from groups comprising at least one amine function optionally bearing at least one of hydrophobic groups and groups L";
L, L' and L", which may be identical or different, are chosen from groups derived from an diisocyanate;
P and P', which may be identical or different, are chosen from groups comprising an amine function optionally bearing a hydrophobic group;
Y is chosen from hydrophilic groups;
r is an integer ranging from 1 to 100;
a, m and p, which may be identical or different, range from 0 to 1,000; wherein
the polymer comprises at least one of protonated amine functions and quaternized amine functions and at least one hydrophobic group.
17. The composition according to claim 16, wherein r is an integer ranging from 1 to 50.
18. The composition according to claim 16, wherein r is an integer ranging from 1 to 25.
19. The composition according to claim 1, wherein the at least one associative polymer is present in the composition in an amount ranging from 0.05% to 10% by weight, relative to the total weight of the composition.
20. The composition according to claim 19, wherein the at least one associative polymer is present in the composition in an amount ranging from 0.1% to 5% by weight, relative the total weight of the composition.
21. The composition according to claim 1, wherein the ratio by weight of the at least one compound chosen from fatty acid esters and metal oxides to the at least one associative polymer ranges from 0.5 to 5.
22. The composition according to claim 1, wherein the at least one oxidation dye is chosen from oxidation bases and couplers.
23. The composition according to claim 22, wherein the at least one oxidation dye is chosen from oxidation bases.
24. The composition according to claim 22, wherein the oxidation bases are chosen from ortho- and para-phenylenediamines, double bases, ortho- and para-aminophenols, heterocyclic bases, and the acid addition salts thereof.

25. The composition according to claim 24, wherein the para-phenylenediamines are chosen from the compounds of structure (XI) below:

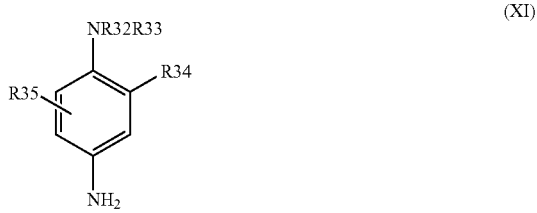

in which:
- R32 is chosen from a hydrogen atom, $C_1$–$C_4$ alkyl radicals, $C_1$–$C_4$ monohydroxyalkyl radicals, $C_2$–$C_4$ polyhydroxyalkyl radicals, $(C_1$–$C_4)$alkoxy$(C_1$–$C_4)$alkyl radicals, and $C_1$–$C_4$ alkyl radicals substituted with at least one of nitrogenous, phenyl, and 4'-aminophenyl groups;
- R33 is chosen from a hydrogen atom, $C_1$–$C_4$ alkyl radicals, $C_1$–$C_4$ monohydroxyalkyl radicals, $C_2$–$C_4$ polyhydroxyalkyl radicals, $(C_1$–$C_4)$alkoxy$(C_1$–$C_4)$alkyl radicals, and $C_1$–$C_4$ alkyl radicals substituted with at least one nitrogenous group; or
- R32 and R33 may form, with the nitrogen atom to which they are attached, a 5- or 6-membered nitrogen heterocycle optionally substituted with at least one of alkyl, hydroxyl, and ureido groups;
- R34 is chosen from a hydrogen atom, halogen atoms, $C_1$–$C_4$ alkyl radicals, sulpho radicals, carboxyl radicals, $C_1$–$C_4$ monohydroxyalkyl radicals, $C_1$–$C_4$ hydroxyalkoxy radicals, acetylamino$(C_1$–$C_4)$alkoxy radicals, mesylamino$(C_1$–$C_4)$alkoxy radicals, and carbamoylamino$(C_1$–$C_4)$alkoxy radicals; and
- R35 is chosen from a hydrogen atom, halogen atoms, and $C_1$–$C_4$ alkyl radicals.

26. The composition according to claim 25, wherein R34 is a chlorine atom.

27. The composition according to claim 24, wherein the double bases are chosen from compounds of formula (X) below:

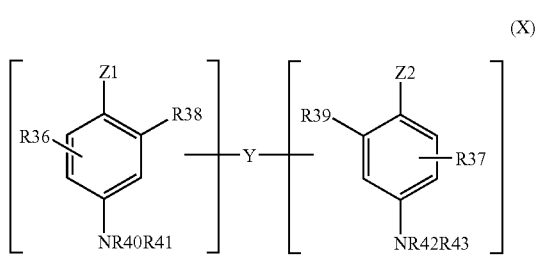

in which:
- Z1 and Z2, which may be identical or different, are chosen from hydroxyl radicals and —$NH_2$ radicals, optionally substituted with at least one of $C_1$–$C_4$ alkyl radicals and a linker arm Y;
- the linker arm Y is chosen from linear and branched alkylene chains having from 1 to 14 carbon atoms, optionally interrupted by and optionally terminated with at least one entity chosen from nitrogenous groups and heteroatoms, and optionally substituted with at least one of hydroxyl radicals and $C_1$–$C_6$ alkoxy radicals;
- R36 and R37 are chosen from a hydrogen atom, halogen atoms, $C_1$–$C_4$ alkyl radicals, $C_1$–$C_4$ monohydroxyalkyl radicals, $C_2$–$C_4$ polyhydroxyalkyl radicals, $C_1$–$C_4$ aminoalkyl radicals, and a linker arm Y;
- R38, R39, R40, R41, R42 and R43, which may be identical or different, are chosen from a hydrogen atom, a linker arm Y, and $C_1$–$C_4$ alkyl radicals;

it being understood that the compounds of formula (X) contain only one linker arm Y per molecule.

28. The composition of claim 27, wherein the at least one heteroatom is chosen from oxygen, sulfur, and nitrogen atoms.

29. The composition according to claim 24, wherein the para-aminophenols are chosen from the compounds of formula (XI) below:

in which:
- R44 is chosen from a hydrogen atom, halogen atoms, $C_1$–$C_4$ alkyl radicals, $C_1$–$C_4$ monohydroxyalkyl radicals, $(C_1$–$C_4)$alkoxy$(C_1$–$C_4)$alkyl radicals, $C_1$–$C_4$ aminoalkyl radicals, and hydroxy$(C_1$–$C_4)$alkylamino $(C_1$–$C_4)$alkyl radicals;
- R45 is chosen from a hydrogen atom, halogen atoms, $C_1$–$C_4$ alkyl radicals, $C_1$–$C_4$ monohydroxyalkyl radicals, $C_2$–$C_4$ polyhydroxyalkyl radicals, $C_1$–$C_4$ aminoalkyl radicals, $C_1$–$C_4$ cyanoalkyl radicals, and $(C_1$–$C_4)$alkoxy$(C_1$–$C_4)$alkyl radicals; and
- R46 is chosen from a hydrogen atom and $C_1$–$C_4$ alkyl radicals.

30. The composition according to claim 29, wherein the halogen atom is fluorine.

31. The composition according to claim 24, wherein the heterocyclic bases are chosen from pyridine derivatives, pyrimidine derivatives, and pyrazole derivatives.

32. The composition according to claim 23, wherein the oxidation base is present In an amount ranging from 0.0005% to 12% by weight, relative to the total weight of the composition.

33. The composition according to claim 32, wherein the oxidation base is present in an amount ranging from 0.005% to 8% by weight, relative to the total weight of the composition.

34. The composition according to claim 22, wherein the couplers are chosen from meta-phenylenediamines, meta-aminophenols, meta-diphenols, heterocyclic couplers, and the acid addition salts thereof.

35. The composition according to claim 22, wherein the couplers are present In an amount ranging from 0.0001% to 10% by weight, relative to the total weight of the composition.

36. The composition according to claim 35, wherein the couplers are present in an amount ranging from 0.005% to 5% by weight, relative to the total weight of the composition.

37. The composition according to claim 24, wherein the acid addition salts of the oxidation barn are chosen from hydrochloride, hydrobromides, sulphates, tartrates, lactates, and acetates.

38. The composition according to claim 1, further comprising at least one direct dye.

39. The composition according to claim 1, wherein the at least one fatty alcohol is chosen from oxyalkylenated and glycerolated fatty alcohols.

40. The composition according to claim 39, wherein the oxyalkylenated fatty alcohol is linear or branched, saturated or unsaturated and contains 10 to 20 carbon atoms and 2 to 40 ethylene oxide groups.

41. The composition according to claim 39, wherein the glycerolated fatty alcohol is linear or branched, saturated or unsaturated and contains 8 to 40 carbon atoms and 1 to 30 glycerol groups.

42. The composition according to claim 1, wherein the at least one fatty alcohol is present in an amount ranging from 0.05% to 30% by weight, relative to the total weight of the composition.

43. The composition according to claim 42, wherein the at least one fatty alcohol is present in an amount ranging from 0.5% to 20% by weight, relative to the total weight of the composition.

44. The composition according to claim 1, further comprising at least one substantive polymer chosen from amphoteric and cationic polymers different from the at least one associative polymer.

45. The composition according to claim 44, wherein the at least one substantive polymer is a homopolymer of dimethyldiallylammonium chloride.

46. The composition according to claim 44, wherein the at least one substantive polymer is a polymer of quaternary polyammonium comprising at least one repeating unit corresponding to formula (W) below:

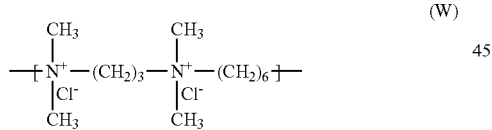

47. The composition according to claim 44, wherein the at least one substantive polymer is a polymer of quaternary polyammonium comprising at least one repeating unit corresponding to formula (U) below:

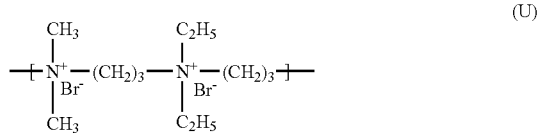

48. The composition according to claim 44, wherein the at least one substantive polymer is chosen from cationic and amphoteric polymers, and is present in an amount ranging from 0.01% to 10% by weight, relative to the total weight of the composition.

49. The composition according to claim 48, wherein the at least one substantive polymer is chosen from cationic and amphoteric polymers, and is present in an amount ranging from 0.05% to 5% by weight, relative to the total weight of the composition.

50. The composition according to claim 49, wherein the at least one substantive polymer is chosen from cationic and amphoteric polymers, and is present in an amount ranging from 0.1% to 3% by weight, relative to the total weight of the composition.

51. The composition according to claim 1, further comprising at least one surtactant chosen from anionic, amphoteric, non-ionic, zwitterionic, and cationic surfactants.

52. The composition according to claim 51, wherein the at least one surfactant is non-ionic.

53. The composition according to claim 51, wherein the at least one surfactant is present in an amount ranging from 0.01% to 40% by weight, relative to the total weight of the composition.

54. The composition according to claim 53, wherein the at least one surfactant is present in an amount ranging from 0.5% to 30% by weight, relative to the total weight of the composition.

55. The composition according to claim 1, further comprising at least one supplementary thickener.

56. The composition according to claim 55, wherein the at least one supplementary thickener is chosen from cellulosic thickeners, guar gum derivatives, gums of microbial origin, and synthetic thickeners.

57. The composition according to claim 55, wherein the at least one supplementary thickener is present in an amount ranging from 0.01% to 10% by weight, relative to the total weight of the composition.

58. The composition according to claim 1, further comprising at least one reducing agent in an amount ranging from 0.05% to 1.5% by weight, relative to the total weight of the composition.

59. A ready-to-use composition for the oxidation dyeing of keratin fibers, comprising, in a medium suitable for dyeing,
   a) at least one oxidation dye;
   b) at least one fatty alcohol;
   c) at least one associative polymer chosen from cationic polyurethanes;
   d) at least one compound chosen from fatty acid esters and metal oxides; and
   e) at least one oxidizing agent,
   wherein the ratio by weight of the at least one compound chosen from fatty acid esters and metal oxides to the at least one associative polymer ranges from 0.1 to 10.

60. The composition according to claim 59, wherein the at least one oxidizing agent is chosen from hydrogen peroxide, urea peroxide, alkali metal bromides, ferricyanides, persalts, and redox enzymes together where appropriate with the respective donor or co-factor thereof.

61. The composition according to claim 60, wherein the at least one oxidizing agent is hydrogen peroxide.

62. The composition according to claim 61, wherein the at least one oxidizing agent is an aqueous hydrogen peroxide solution whose titre ranges from 1 to 40 volumes.

63. The composition according to claim 62, wherein the pH of the aqueous $H_2O_2$ solution ranges from 4 to 11.

* * * * *

UNITED STATES PATENT AND TRADEMARK OFFICE
CERTIFICATE OF CORRECTION

PATENT NO. : 7,204,859 B2 Page 1 of 1
APPLICATION NO. : 10/728890
DATED : April 17, 2007
INVENTOR(S) : François Cottard et al.

It is certified that error appears in the above-identified patent and that said Letters Patent is hereby corrected as shown below:

Column 43, line 45, "l" should read --1--.

Column 44, line 56, "relative the" should read --relative to the--.

Column 45, line 5, "(Xl)" should read --(XI)--.

Column 46, line 20, "(Xl)" should read --(XI)--.

Column 46, line 52, "In" should read --in--.

Column 46, line 65, "In" should read --in--.

Column 47, line 3, "0.005%to5%" should read --0.005% to 5%--.

Column 47, line 6, "barn" should read --bases--.

Column 47, line 7, "hydrochloride," should read --hydrochlorides,--.

Signed and Sealed this

Nineteenth Day of June, 2007

JON W. DUDAS
*Director of the United States Patent and Trademark Office*